United States Patent [19]
Williams

[11] Patent Number: 6,080,422
[45] Date of Patent: Jun. 27, 2000

[54] METHODS OF ANGIOPLASTY AND CARDIAC CATHETERIZATION

[75] Inventor: Kevin Jon Williams, Wynnewood, Pa.

[73] Assignee: Talaria Therapeutics, Inc., West Conshohocken, Pa.

[21] Appl. No.: 08/731,256

[22] Filed: Oct. 11, 1996

Related U.S. Application Data

[60] Provisional application No. 60/005,090, Oct. 11, 1995.

[51] Int. Cl.[7] .......................... A61K 9/127; A61K 31/685
[52] U.S. Cl. ............................ 424/450; 514/77; 514/78; 514/824
[58] Field of Search ............................. 424/450; 514/77, 514/78, 824

[56] References Cited

U.S. PATENT DOCUMENTS

| | | | |
|---|---|---|---|
| 4,812,314 | 3/1989 | Barenholz et al. | 424/450 |
| 5,077,056 | 12/1991 | Bally et al. | 424/450 |
| 5,204,112 | 4/1993 | Hope et al. | 124/450 |
| 5,252,263 | 10/1993 | Hope et al. | 264/4.3 |
| 5,376,452 | 12/1994 | Hope et al. | 428/402.2 |
| 5,489,611 | 2/1996 | Lee et al. | 514/557 |
| 5,556,637 | 9/1996 | Hager et al. | 424/450 |
| 5,622,715 | 4/1997 | Barenholz et al. | 424/450 |
| 5,741,514 | 4/1998 | Barenholz et al. | 424/450 |
| 5,741,517 | 4/1998 | Hager et al. | 424/450 |

FOREIGN PATENT DOCUMENTS

| | | | |
|---|---|---|---|
| 0 234 919 B1 | 9/1987 | European Pat. Off. | A61K 9/50 |
| 0 461 559 B1 | 12/1991 | European Pat. Off. | A61K 31/685 |
| 40 18 767 A1 | 12/1991 | Germany | A61K 31/685 |
| WO 95/23592 | 9/1995 | WIPO | A61K 9/127 |

OTHER PUBLICATIONS

Daida et al., Prevention Of Restenosis After Percutaneous Transluminal Coronary Angioplasty By Reducing Lipoprotein (a) Levels With Low–Density Lipoprotein Apheresis, Jun. 1, 1994, vol. 73, No. 15, pp. 1037–1040.

Desmarais et al., Elevated Serum Lipoprotein(a) Is A Risk Factor For Clinical Recurrence After Coronary Balloon Angioplasty, Cirulation, vol. 91, No. 5, Mar. 1, 1995, pp. 1403–1409.

Groop et al., Lipoprotein(a) In Type 1 Diabetic Patients With Renal Disease, Original Articles, May 11, 1994, pp. 961–967.

Kokoglu et al., Elevated Serum Lp(a) Levels In The Early And Advanced Stages Of Breast Cancer, Cancer Biochem, Biophys., 1994, vol. 14, pp. 133–136.

Kuriyama et al., Low Levels Of Serum Apolipoprotein A I And A II In Senile Dementia, The Japanese Journal Of Psychiatry And Neurology, vol. 48, No. 3, 1994, pp. 589–593.

Sachs, Bernard A., et al., In Vivo Effects Of Inositol Phosphatide (Lipositol) In Serum Lipids And Atherosclerosis Of Hyperlipemic Rabbits, J. Appl. Physiol., 15:983–986, 1960.

Takahashi et al., Increased Concentrations Of Serum Lp(a) Lipoprotein In Patients With Primary Gout, Annals Of The Rheumatic Diseases 1995, vol. 54, pp. 90–93.

Tenda et al., The Relationship Between Serum Lipoprotein(a) And Restenosis After Initial Elective Percutaneous Transluminal Coronary Angioplasty, Japanese Circulation Journal, vol. 57, Aug., 1993, pp. 789–795.

Williams et al., Uptake of Endogenous Cholesterol By A Synthetic Lipoprotein, Elsevier Science Publishers B.V. (Biomedical Division), 1986, pp. 183–194.

Yamamoto et al., Serum Lipoprotein (a) Levels Before And After Subtotal Thyroidectomy In Subjects With Hyperthyroidism, Metabolism, vol. 44, No. 1 (Jan.), 1995, pp. 4–7.

Bangham et al., "Diffusion of Univalent Ions across the Lamallae of Swollen Phospholipids" *J.Mol.Biol.* pp 238–252 (May 6, 1965).

Davidson, et al., "Association and release of prostaglandin EI from liposomes" *Biochim. Biophys. Acta* 1327(1), pp 97–106 (1997).

Davidson, W.S., et al., "The effect of high density lipoprotein phospholipid acyl chain composition on the efflux of cellular free cholesterol" *J. Biol. Chem.* 270(11), 5882–590 (Mar. 1995).

De Caterina and Lenzi, "Prevention and therapy of vascular damage and endothelial dysfunction with hypocholesteremic agents" *G. Ital. Cardiol.* 28(2), 168–177 (Feb. 1998).

(List continued on next page.)

*Primary Examiner*—Kimberly Jordan
*Attorney, Agent, or Firm*—Michael Best & Friedrich

[57] ABSTRACT

The present invention provides an improved mode of operation of an apparatus for angioplasty or cardiac catheterization, apparatus for angioplasty and cardiac catheterization, and method of angioplasty or cardiac catheterization. The improvement and improved mode of operation includes the step of administering a therapeutically effective amount of a lipid acceptor during angioplasty or cardiac catheterization of a subject with the apparatus or component thereof. The lipid acceptor is selected from the group consisting of a large liposome comprised of phospholipids substantially free of sterol and small acceptors. The effective period of time is in the range of about less than 1 minute to about two years from the time of the angioplasty or cardiac catheterization. The improved angioplasty or cardiac catheterization apparatus includes means for administering a therapeutically effective amount of a lipid acceptor, and optional co-administration means for administering the lipid acceptor and a diagnostic agent. The improved mode of operating an angioplasty or cardiac catheterization apparatus includes administering a therapeutically effective amount of a lipid acceptor from the apparatus or component thereof into a vessel of a subject by administration means. The invention further provides a method of diagnosing a side-effect of reverse transport of cholesterol from peripheral tissues to the liver in vivo accompanying parenteral administration of a multiplicity of large liposomes and small liposomes during a treatment period. The method includes the step of periodically assaying plasma atherogenic lipoprotein concentrations with an assay to obtain an assayed atherogenic lipoprotein concentration.

29 Claims, 28 Drawing Sheets

OTHER PUBLICATIONS

Farnier and Davignon, "Current and future treatment of hyperlipidemia: the role of statins" *Am. J. Cardiol.* 82(4B), 3J–10J (Aug. 27, 1998).

Gould, "New concepts and paradigms in cardiovascular medicine: the noninvasive management of coronary artery disease" *Am. J. Med.* 104(6A), 2S–175 (Jun. 22, 1998).

Hernandez–Perera, et al., "Effects of the 3 –hydroxy–3 –methylglutaryl–CoA reductase inhibitors, atorvastatin and simvastatin, on the expression of endothelin– 1 and endothelial nitric oxide synthase in vascular endothelial cells" *J. Clin. Invest.* 101(12), pp 2711–2719 (Jun. 15, 1998).

Isele, et al., "Pharmacokinetics and body distribution of liposomal zinc phthalocyanine in tumor–bearing mice: influence of aggregation state, particle size, and composition" *J. Pharm. Sci.* 84(2), pp 166–173 (Feb. 1995).

Luscher, et al., "Lipids and endothelial function: effects of lipid–lowering and other therapeutic interventions" *Curr. Opin. Lipidol.* 7(4), 234–240 (Aug. 1996).

Ravid, et al., "Main risk factors for nephropathy in type 2 diabetes mellitus are plasma cholesterol levels, mean blood pressure, and hyperglycemia" *Arch. Intern. Med.* 158(9), pp 998–1004 (May 11, 1998).

Rodrigueza et al., Large versus small unilamellar vesicles mediate reverse cholesterol transport in vivo into two distinct hepatic metabolic pools. Implications for the treatment of atherosclerosis. *Arteriolscle. Thromb. Vasc. Biol.* 17(10), 2132–2139 (Oct. 1997).

Rodrigueza, et al., Cholesterol mobilization and regression of atheroma in cholestrol–fed rabbits inducted by large unilamellar vesicles. *Biochim. Biophys. Acta* 1368(2), pp 306–320 (Jan. 19, 1998).

Sparks, et al., "Effect of cholesterol on the charge and structure of apolipoprotein A–I in recombinant high density lipoprotein particles" *J. Biol. Chem.* 268(31), 23250–23257 (Nov. 5, 1993).

Sparks, et al., "The charge and structural stability of apolipoprotein A–I in discoidal and spherical recombinant high density lipoprotein particles" *J. Biol. Chem.* 267(36), 25839–25847 (Dec. 25, 1992).

Tricerri, et al., "Conformation of apolipoprotein AI in reconstituted lipoprotein particles and particle–membrane interaction: effect of cholesterol" *Biochim. Biophys. Acta* 1391(1), pp 67–78 (Mar. 6, 1998).

A.I. Soloviev, et al., Phospholipid Vesicles (Liposomes) Restore Endothelium–Dependent Cholinergic Relaxation In Thoracic Aorta From Spontaneously Hypertensive Rats, Journal of Hypertension 1993; vol. 11; No. 6; pp. 623–627.

Adams CWM, Abdulla YH, Bayliss OB, Morgan RS: Modification of aortic atheroma and fatty liver in cholesterol–fed rabbits by intravenous injection of saturated and polyunsaturated lecithins. J Pathol Bacteriol 94:77–87, 1967.

Altman RFA, de Mendonia JM, Schaeffer GMV, Ramos de Souza J, Bandoli JG, da Silva DJ, Lopes CRN: Phospholipids in experimental atherosclerosis. Arzneim Forsch 24:11–16, 1974.

Aviram M, Williams KJ, Deckelbaum RJ: Macrophage cholesterol removal by triglyceride–phospholipid emulsions. Biochem Biophys Res Commun 155:709–713, 1988.

Aviram M, Williams KJ, McIntosh RA, Carpentier YA, Tall AR, Deckelbaum RJ: Intralipid infusion abolishes ability of human serum to cholesterol–load cultured macrophages. Arteriosclerosis 9:67–75, 1989.

Bally MB, Hope MJ, Mayer LD, Madden TD, Cullis PR: Novel procedures for generating and loading liposomal systems. In: Gregoriadis G, ed. *Liposomes as drug carriers: recent trends and progress.* Chichester, England: John Wiley & Sons Ltd., 1988. pp. 841–853.

Bialecki RA, Tulenko TN, Colucci WS: Cholesterol enrichment increases basal and agonist–stimulated calcium influx in rat vascular smooth muscle cells. J Clin Invest 88:1894–1900, 1991.

Blaton V, Declercq B, Vandamme D, Soetewey F, Peeters H: The human plasma lipids and lipoproteins under influence of EPL–therapy. In: Peeters H, ed. *Phosphatidylcholine.* Berlin: Springer–Verlag, 1976 pp. 125–132.

Byers SO, Friedman M: Effect of infusions of phosphatides upon the atherosclerotic aorta in situ and as an ocular aortic implant. J Lipid Res 1:343–348, 1960.

Campanacci L, Guarnieri G, Faccini L, Bellini G: Response of plasma lipid fractions to the administration of exogenous phospholipids. Arzneimittelforschung 25:1306–1308, 1975.

Ciammaichella A, Solitro A, Arcuri P: La fosfatidilcolina polinsatura (EPL) nel trattamento delle affezioni aterosclerotiche cerebrali e degli arti inferiori. Clin Ter 74:55–62, 1975.

Ellens H, Morselt H, Scherphof G: In vivo fate of large unilamellar sphingomyelin–cholesterol liposomes after intraperitoneal and intravenous injection into rats. Biochim Biophys Acta 674:10–18, 1981.

Friedman M, Byers SO, Rosenman RH: Resolution of aortic atherosclerotic infiltration in the rabbit by phosphatide infusion. Proc Soc Exp Biol Med 95:586–588, 1957.

Howard AN, Patelski J, Bowyer DE, Gresham GA: Atherosclerosis induced in hypercholesterolaemic baboons by immunological injury; and the effects of intravenous polyunsaturated phosphatidyl choline. Atherosclerosis 14:17–29, 1971.

Kobashigawa JA, Katznelson S, Laks H, Johnson JA, Yeatman L, Wang XM, Chia D, Terasaki PI, Sabad A, Cogert GA, Trosian K, Hamilton MA, Moriguchi JD, Kawata N, Hage A, Drinkwater DC, Stevenson LW: Effect of pravastatin on outcomes after cardiac transplantation. New Engl J Med 333:621–627, 1995.

Krack G, Viglino G, Cavalli PL, Gandolfo C, Magliano G, Cantaluppi A, Peluso F: Intraperitoneal administration of phosphatidylcholine improves ultrafiltration in continuous ambulatory peritoneal dialysis patients. Perit Dial Int 12:359–364, 1992.

Mauk MR, Gamble RC: Stability of lipid vesicles in tissues of the mouse: a gamma–ray perturbed angular correlation study. Proc Natl Acad Sci (USA) 76:765–769, 1979.

Maurukas J, Thomas RG: Treatment of experimental atherosclerosis in the rabbit with L,D. alpha (dimyristoyl) lecithin. J Lab Clin Med 56:30–37, 1960.

Mihail A, Popescu P, Idu SM, Petrescu X, Cociumian L, Mihai N: The coronary syndrome in two cases of essential familial hypercholesterolemia (the therapeutic effect of polyene–phosphatidyl–choline). Rev Roum Med Intern 10:225–233, 1973.

Miyazaki A, Sakai M, Suginohara Y, Hakamata H, Sakamoto Y, Morikawa W, Horiuchi S: Acetylated low density lipoprotein reduces its ligand activity for the scavenger receptor after interaction with reconstituted high density lipoprotein. J Biol Chem 269:5264–5269, 1994.

Patelski J, Bowyer DE, Howard AN, Jennings IW, Thorne CJR, Gresham GA: Modification of enzyme activities in experimental atherosclerosis in the rabbit. Atherosclerosis 12:41–53, 1970.

Plane F, Bruckdorfer KR, Kerr P, Steuer A, Jacobs M: Oxidative modification of low–density lipoproteins and the inhibition of relaxations mediated by endothelium–derived nitric oxide in rabbit aorta. Br J Pharmacol 105:216–222, 1992.

Rodrigueza WV, Hope MJ, Williams KJ: Large unilamellar vesicles (LUV) efficiently mobilize tissue cholesterol to the liver yet do not provoke a rise in plasma concentrations of cholesteryl ester–rich atherogenic lipoproteins. 18th Canadian Lipoprotein Conference Oct. 17, 1994.(Abstract).

Rodrigueza WV, Pritchard PH, Hope MJ: The influence of size and composition on the cholesterol mobilizing properties of liposomes in vivo. Biochim Biophys Acta 1153:9–19, 1993.

Sahni R, Maniet AR, Voci G, Banka VS: Prevention of restenosis by lovastatin after successful coronary angioplasty. Am Heart J 121:1600–1608, 1991.

Schmidt K, Klatt P, Graier WF, Kostner GM, Kukovetz WR: High–density lipoprotein antagonizes the inhibitory effects of oxidized low–density lipoprotein and lysolecithin on soluble guanylyl cyclase. Biochem Biophys Res Commun 182:302–308, 1992.

Shmeeda H, Petkova D, Barenholz Y: Cholesterol distribution in rat heart myocytes. Am J Physiol 268:H759–H766, 1995.

Stafford WW, Day CE: Regression of atherosclerosis effected by intravenous phospholipid. Artery 1:106–114, 1975.

Stroes ES, Koomans HA, de Bruin TW, Rabelink TJ: Vascular function in the forearm of hypercholesterolaemic patients off and on lipid–lowering medication. Lancet 346:467–471, 1995.

Stuart MJ, Gerrard JM, White JG: Effect of cholesterol on production of thromboxane b2 by platelets in vitro. New Engl J Med 302:6–10, 1980.

Sugiyama S, Kugiyama K, Matsumura T, Suga S, Itoh H, Nakao K, Yasue H: Lipoproteins regulate C–type natriuretic peptide secretion from cultured vascular endothelial cells. Arterioscler Thromb Vasc Biol 15:1968–1974, 1995.

Tall AR, Tabas I, Williams KJ: Lipoprotein–liposome interactions. Methods Enzymol 128:647–657, 1986.

Thompson GR, Jadhav A, Nava M, Gotto AM,Jr.: Effects of intravenous phospholipid on low density lipoprotein turnover in man. Eur J Clin Invest 6:241–248, 1976.

Waligora Z, Patelski J, Brown BD, Howard AN: Effect of a hypercholesterolaemic diet and a single injection of polyunsaturated phosphatidyl choline solution on the activities of lipolytic enzymes, acyl–CoA synthetase and acyl–CoA cholesterol acyl–transferase in rabbit tissues. Biochem Pharmacol 24:2263–2267, 1975.

Williams KJ, Brocia RW, Fisher EA: The unstirred water layer as a site of control of apolipoprotein B secretion. J Biol Chem 265:16741–16744, 1990.

Williams KJ, Scanu AM: Uptake of endogenous cholesterol by a synthetic lipoprotein. Biochim Biophys Acta 875:183–194, 1986.

Williams KJ, Tall AR: Interactions of liposomes with lipoproteins: relevance to drug delivery systems and to the treatment of atherosclerosis. In: Gregoriadis G, ed. Liposomes as drug carriers: recent trends and progress. Chichester, England: John Wiley & Sons Ltd., 1988. pp. 93–111.

Williams KJ, Tall AR, Bisgaier C, Brocia R: Phospholipid liposomes acquire apolipoprotein E in atherogenic plasma and block cholesterol loading of cultured macrophages. J Clin Invest 79:1466–1472, 1987.

Williams KJ, Tall AR, Tabas I, Blum C: Recognition of vesicular lipoproteins by the apolipoprotein B,E receptor of cultured fibroblasts. J Lipid Res 27:892, 1986.

Williams KJ, Vallabhajosula S, Rahman IU, Donnelly TM, Parker TS, Weinrauch M, Goldsmith SJ: Low density lipoprotein receptor–independent hepatic uptake of a synthetic, cholesterol–scavenging lipoprotein: implications for the treatment of receptor–deficient atherosclerosis. Proc Natl Acad Sci (USA) 85:242–246, 1988.

Williams KJ, Werth VP, Wolff JA: Intravenously administered lecithin liposomes: a synthetic antiatherogenic lipid particle. Perspect Biol Med 27:417–431, 1984.

Yechiel E, Barenholz Y: Relationships between membrane lipid composition and biological properties of rat myocytes. Effects of aging and manipulation of lipid composition. J Biol Chem 260:9123–9131, 1985.

| LUV-SUV #2 | | | Hepatic mRNA content (pg/ug) | | | | | | |
|---|---|---|---|---|---|---|---|---|---|
| Rabbit # | Treatment | CETP | HMG-CoA R | LDL R | 7a-hydroxylase | LDL ChE, day 1 | LDL ChE, day 3 | LDL ChE, day 5 | LDL ChE, day 6 |
| 1 | (A) PBS | 2.87 | 0.54 | 4.27 | 0.56 | 7.4 | 7.1 | 5.2 | 6.5 |
| 2 | (A) PBS | 5.63 | 0.55 | 5.38 | 0.39 | 18.1 | 11.8 | 6.2 | 9.7 |
| 3 | (A) PBS | 5.34 | 0.39 | 8.93 | 0.74 | 8.5 | 8.9 | 4.4 | 8.7 |
| 4 | (A) PBS | 5.04 | 0.55 | 5.49 | 0.82 | 14.1 | 14.1 | 6.8 | 8.6 |
| | Mean | 4.72 | 0.51 | 6.02 | 0.83 | 11.53 | 10.48 | 6.15 | 8.38 |
| | SEM | 0.63 | 0.04 | 1.01 | 0.10 | 2.12 | 1.55 | 0.98 | 0.67 |
| 5 | (B) LUV | 3.15 | 0.58 | 7.23 | 0.63 | 25.3 | 14.9 | 13.6 | 10.5 |
| 6 | (B) LUV | 3.02 | 0.47 | 8.15 | 0.58 | 14.0 | 15.9 | 10.8 | 8.2 |
| 7 | (B) LUV | 2.52 | 0.58 | 4.81 | 0.83 | 28.3 | 22.5 | 21.3 | 22.4 |
| 8 | (B) LUV | 2.68 | 0.58 | 7.37 | 0.94 | 17.5 | 21.8 | 13.4 | 9.5 |
| | Mean | 2.84 | 0.55 | 6.89 | 0.75 | 21.28 | 16.78 | 14.78 | 12.85 |
| | SEM | 0.15 | 0.03 | 0.72 | 0.08 | 3.33 | 1.96 | 2.27 | 3.28 |
| | t vs. PBS | 2.910 | 0.939 | 0.703 | 0.919 | 2.473 | 3.318 | 3.506 | 1.275 |
| 13 | SUV + LUV | 3.18 | 0.50 | 5.28 | 0.51 | 11.9 | 34.0 | 20.1 | 22.2 |
| 10 | (C) SUV | 5.64 | 0.38 | 3.98 | 0.30 | 21.1 | 45.3 | 15.3 | 46.3 |
| 11 | (C) SUV | 3.39 | 0.29 | 3.67 | 0.42 | 10.0 | 36.3 | 59.6 | 42.7 |
| 12 | (C) SUV | 3.00 | 0.13 | 3.34 | 0.63 | 17.8 | 31.8 | 45.5 | 22.3 |
| | Mean w/o #13 | 4.01 | 0.27 | 3.66 | 0.45 | 16.30 | 37.80 | 40.13 | 37.10 |
| | SEM w/o #13 | 0.02 | 0.07 | 0.18 | 0.10 | 3.28 | 3.97 | 13.07 | 7.47 |
| | t vs. PBS | 0.686 | 2.903 | 2.295 | 1.304 | 1.220 | 6.414 | 2.594 | 3.628 |
| | t vs. LUV | 1.397 | 3.660 | 4.328 | 2.301 | 1.963 | 4.296 | 1.912 | 2.98 |
| | Mean w/ #13 | 3.80 | 0.33 | 4.07 | 0.47 | 15.20 | 38.86 | 35.13 | 33.38 |
| | SEM w/ #13 | 0.62 | 0.06 | 0.42 | 0.07 | 2.57 | 2.96 | 10.51 | 8.48 |
| | t vs. PBS | 1.041 | 2.091 | 1.781 | 1.369 | 1.103 | 7.890 | 2.748 | 3.848 |
| | t vs. LUV | 1.512 | 2.763 | 3.369 | 2.554 | 1.445 | 8.085 | 1.893 | 2.856 |

FIG. 2

*Indicates column of interest

Key points about LUV and atherosclerosis

1) Practical: Straight forward to manufacture

Non-toxic at very high doses

2) Mechanistic: Liposomes promote reverse cholesterol transport *in vivo*

LUV are the optimal preparation

FIG. 9

- Effectiveness in humans

- Therapeutic targets

Lipid-rich, rupture-prone plaques
    Critical Stenosis
    Post-angioplasty re-stenosis
    Atherosclerosis in general

FIG. 18

METHODS OF ANGIOPLASTY AND CARDIAC CATHETERIZATION

CONTINUING DATA

This application is a continuation in part regular patent application of pending U.S. provisional patent application Ser. No. 60/005,090 filed by Kevin Jon Williams, a citizen of the United States, residing at 425 Wister Road, Wynnewood, Pa. 19096 on Oct. 11, 1995 entitled "METHOD OF FORCING THE REVERSE TRANSPORT OF CHOLESTEROL FROM PERIPHERAL TISSUES TO THE LIVER IN VIVO WHILE CONTROLLING PLASMA LDL AND COMPOSITIONS THEREFOR." Pending U.S. provisional patent application Ser. No. 60/005,090 filed Oct. 11, 1995 is attached to the instant regular patent application as attachment A. Applicant expressly incorporates attachment A hereto into the instant regular patent application by reference thereto as if fully set forth.

BACKGROUND OF THE INVENTION

Re-obstruction (re-stenosis) of arteries after mechanical or surgical interventions to improve blood flow is a major problem. For example, after coronary angioplasty, re-stenosis rates of 30–40% have been reported. Re-stenosis after surgery to relieve carotid obstructions also occurs, and re-stenosis can occur in other vessels as well. Current treatments for re-stenosis include drugs, such as aspirin or lovastatin, that may somewhat reduce the incidence of restenosis; and the placement of mechanical stents in the vessel lumen to attempt to hold the vessel open. Nevertheless, these methods are at best only partially effective and are often invasive. There exists a need for a simple, effective, non-invasive or minimally invasive approach to reduce re-stenosis or slow its development in patients who undergo mechanical or surgical revascularization procedures.

The process of re-stenosis involves, in part, the proliferation of cells in the arterial wall in response to injury during the revascularization procedure. There is a role for cholesterol and possibly other lipids in this process: high plasma concentrations of LDL and apolipoprotein B, the major protein of atherogenic lipoproteins, are associated with increased carotid re-stenosis (Colyvas et al. *Circulation* 85:1286–1292, 1992), and lovastatin, a cholesterol synthesis inhibitor, somewhat reduces coronary re-stenosis (Sahni et al *Am. Heart J.* 121 [6 pt 1]: 1600–1608, 1996). There exists a need for better methods, devices, and modes of operation of devices to manipulate the lipid content and composition of the arterial wall before, during, and after revascularization procedures, to reduce re-stenosis. Small LDL size has also been associated with increased re-stenosis (Colyvas 1992), and so there exists a need for methods to change LDL composition and size.

The intravenous administration of cholesterol-poor phospholipid vesicles (liposomes) or other particles to transport cholesterol and other exchangeable material from lipoproteins and peripheral tissues, including atherosclerotic arterial lesions, to the liver produces substantial derangements in hepatic cholesterol homeostasis, such as enhanced hepatic secretion of apolipoprotein-B, and suppression of hepatic LDL receptors. The hepatic derangements lead to increased plasma concentrations of LDL and other atherogenic lipoproteins. Increased concentrations of LDL or other atherogenic lipoproteins will accelerate, not retard, the development of vascular complications. Deranged hepatic cholesterol homeostasis can also be manifested by abnormal regulation of other genes, such as a gene for the LDL receptor, a gene for HMG-CoA reductase, a gene for cholesterol 7-alpha hydroxylase, and a gene regulating a function involved in cholesterol homeostasis. There exists a need for methods or compounds that can produce a removal of cholesterol and other exchangeable material from peripheral cells, tissues, organs, and extracellular regions, but without harmfully disrupting hepatic cholesterol homeostasis.

In general, several human conditions are characterized by distinctive lipid compositions of tissues, cells, or membranes. For example, in atherosclerosis, cholesterol (unesterified, esterified, and oxidized forms) and other lipids accumulate in cells and in extracellular areas of the arterial wall and elsewhere. These lipids have potentially harmful biologic effects, for example, by changing cellular functions and by narrowing the vessel lumen, obstructing the flow of blood. Removal of these lipids would provide numerous, substantial benefits. In aging, cells have been shown to accumulate sphingomyelin and cholesterol, which alter cellular functions. These functions can be restored in vitro by removal of these lipids and replacement with phospholipid from liposomes. A major obstacle to performing similar lipid alterations in vivo has been disposition of the lipids mobilized from tissues, cells, extracellular areas, and membranes. Natural (e.g., high-density lipoproteins) and synthetic (e.g., small liposomes) particles that could mobilize peripheral tissue lipids have a substantial disadvantage: they deliver their lipids to the liver in a manner that disturbs hepatic cholesterol homeostasis, resulting in elevations in plasma concentrations of harmful lipoproteins, such as low-density lipoprotein (LDL), a major atherogenic lipoprotein.

The invention described herein provides methods and compositions related the removal of cholesterol and other lipids from peripheral tissues, and otherwise altering peripheral tissue lipids, in patients undergoing revascularization procedures, while controlling plasma concentrations of LDL and other atherogenic lipoproteins and avoiding harmful disruption of hepatic cholesterol homeostasis.

This invention methods and compositions that related to the "reverse" transport of lipids and other exchangeable material from peripheral tissues to the liver in vivo while controlling plasma LDL concentrations. There exists a need for a method of, treatment, and a pharmaceutical composition for forcing the reverse transport of lipids from peripheral tissues to the liver in vivo while controlling plasma LDL concentrations; of regulating hepatic parenchymal cell cholesterol content and metabolism in a cell having at least one gene selected from the group consisting of a gene for an LDL receptor, a gene for HMG-CoA reductase, a gene for cholesterol 7-alpha-hydroxylase, and a gene regulating a function involved in cholesterol homeostasis; and, homeostasis thereof; suppressing hepatic expression of a cholesterol ester transfer protein gene in vivo, whereby plasma LDL and HDL are controlled as a result of said administration; suppressing the rise in plasma LDL concentrations after administration of an agent having small acceptors of cholesterol or other lipids; of diagnosing a side-effect of reverse transport of cholesterol from peripheral tissues to the liver in vivo accompanying parenteral administration of a multiplicity of large liposomes and small liposomes during a treatment period, whereby a side effect of administration of said liposomes is diagnosed and effectively regulated; and, diagnosing and treating a side-effect of reverse transport of lipids from peripheral tissues to the liver in vivo accompanying parenteral administration of a multiplicity of large liposomes and small liposomes during a treatment period. There further exists a need for a system in which patients will have a decreased risk of developing atherosclerosis and/or cellular changes from aging; an improved method of reducing the lipid content of lesions. Other needs and solutions to these needs will be revealed further herein.

The present invention addresses these needs so that diseases and detrimental medical conditions can be treated, controlled or eliminated. The present invention targets a market of millions of individuals world-wide who suffer from medical conditions the present invention is directed to solving. It is an object of the invention to solve the problems enumerated above.

SUMMARY OF THE INVENTION

The present invention provides an improved mode of operation of an apparatus for angioplasty or cardiac catheterization, apparatus for angioplasty and cardiac catheterization, and method of angioplasty or cardiac catheterization. The improved mode of operation includes the step of administering a therapeutically effective amount of a lipid acceptor during angioplasty or cardiac catheterization of a subject with the apparatus or component thereof. The lipid acceptor is selected from the group consisting of a large liposome comprised of phospholipids substantially free of sterol and small acceptors. The effective period of time is in the range of about less than 1 minute to about two years from the time of the angioplasty or cardiac catheterization. The improved angioplasty or cardiac catheterization apparatus includes means for administering a therapeutically effective amount of a lipid acceptor, and optional co-administration means for administering the lipid acceptor and a diagnostic agent. The improved mode of operating an angioplasty or cardiac catheterization apparatus includes administering a therapeutically effective amount of a lipid acceptor from the apparatus or component thereof into a vessel of a subject by administration means disposed on said apparatus. The invention further provides a method of diagnosing a side-effect of reverse transport of cholesterol from peripheral tissues to the liver in vivo accompanying parenteral administration of a multiplicity of large liposomes and small liposomes during a treatment period. The method includes the step of periodically assaying plasma atherogenic lipoprotein concentrations with an assay to obtain an assayed atherogenic lipoprotein concentration. The objects and features of the present invention other than those specifically set forth above, will become apparent in the detailed description of the invention.

It is an object of the invention to provide a simple, effective, non-invasive or minimally invasive approach, method, device, and mode of operation of the device to reduce re-stenosis or slow its development in patients who undergo mechanical or surgical revascularization procedures.

It is a further object of the invention to provide a method, device, and mode of operation of a device to manipulate the lipid content and composition of the arterial wall before, during, and after revascularization procedures, to reduce re-stenosis. It is yet a further object of the invention to provide for a method to change LDL composition and size.

It is yet another object of the invention to provide a method, compound, device and mode of operation of a device that can produce a removal of cholesterol and other exchangeable material from peripheral cells, tissues, organs, and extracellular regions without harmfully disrupting hepatic cholesterol homeostasis. The objects and features of the present invention, other than those specifically set forth above, will become apparent in the detailed description of the invention set forth below.

BRIEF DESCRIPTION OF THE DRAWINGS

FIG. 2 illustrates a table of hepatic mRNA content (pg/$\mu$g) for CETP, HMG-CoAR, LDL receptors, and 7a-hydroxylase; and LDL ChE;

FIG. 9 illustrates key points about LUVs and atherosclerosis;

FIG. 18 illustrates that the compositions and methods of the present invention are effective in humans;

DETAILED DESCRIPTION OF THE INVENTION

Figure 1:
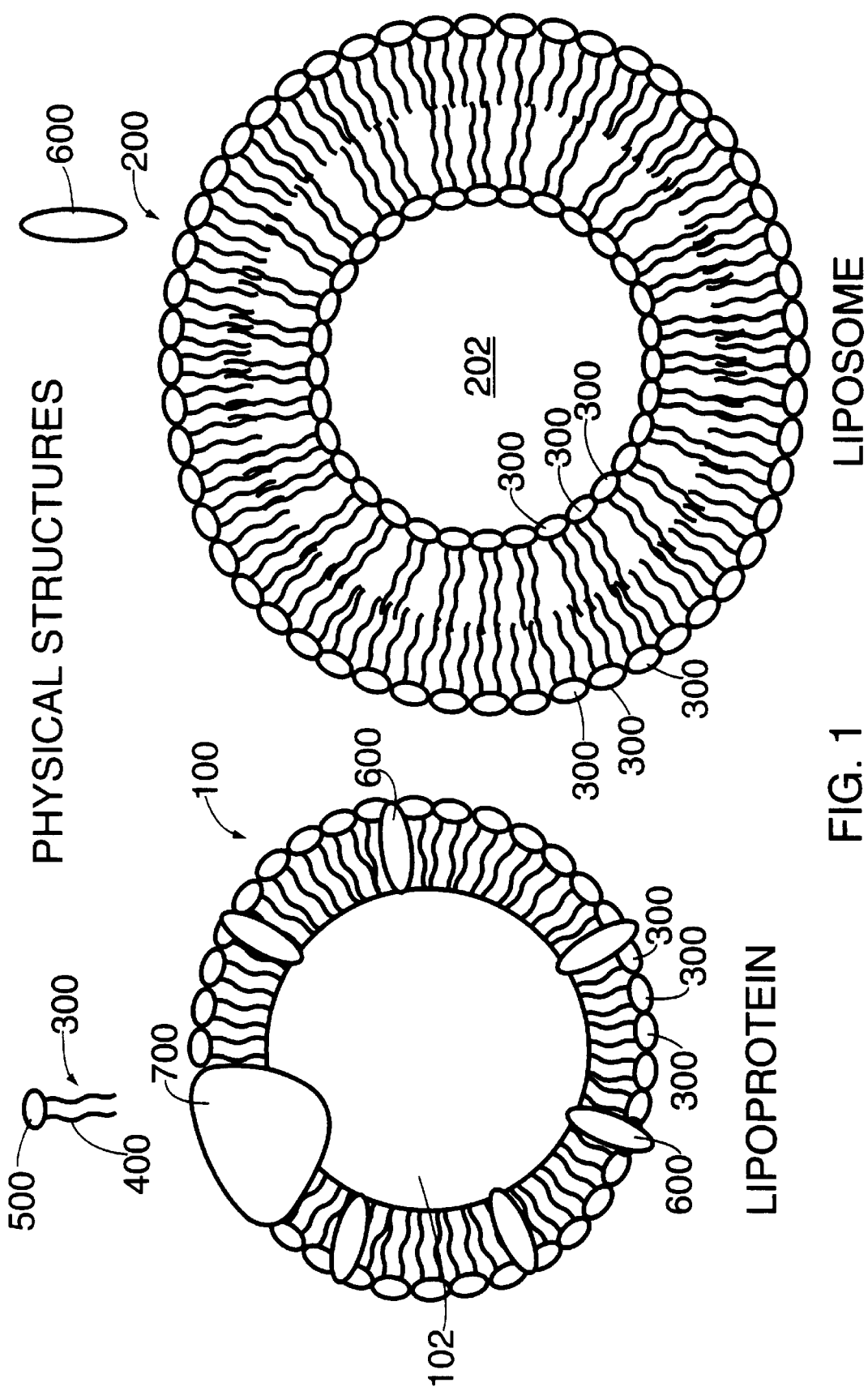
FIG. 1 is a side cross-sectional view of a lipoprotein and a liposome.

FIG. 1 illustrates a schematic illustration of the structure of a normal lipoprotein 100 and a unilamellar liposome 200. Lipoprotein 100 and liposome 200 are comprised of a phospholipid molecule 300. Phospholipid molecules generally have polar head 500 and a fatty acyl chains 400. Molecule 600 represents a molecule of unesterifed cholesterol. Lipoprotein 100 is comprised of a hydrophobic core 102 composed mainly of triglycerides and cholesteryl esters surrounded by a monolayer of phospholipid molecules 300 with their fatty acyl side chains 400 facing the hydrophobic core 102 and their polar heads 500 facing the surrounding aqueous environment (not shown). Unesterified cholesterol 600 is found largely within the phospholipid monolayer. Apolipoprotein 700 is disposed within phospholipid molecules 300. Artificial triglyceride emulsion particles have essentially identical structures, either with or without protein.

Liposome 200 is comprised of phospholipid molecules 300 forming a phospholipid bilayer, e.g. one lamella, either with or without protein, in which fatty acyl side chains 400 face each other, the polar head groups 500 of the outer leaflet face outward to the surrounding aqueous environment (not shown), and the polar head groups 500 of the inner leaflet face inward to the aqueous core 202 of the particle 200. Depending on the composition of particle 200, phospholipid bilayers can have a large capacity for unesterified cholesterol and other exchangeable material and components thereof. As illustrated in FIG. 1 there is no sterol. Typically, such liposomes can pick up unesterified cholesterol from other lipid bilayers, such as cell membranes, and from lipoproteins. Liposomes also pick up proteins and donate phospholipids and other exchangeable material and components thereof. Liposomes can also have multilamellar structures, in which the bilayers are contained within the environment encapsulated by an outer bilayer to form multiple lamellae. The multiple lamellae can be arranged concentrically, like the layers of an onion, or in another variant non-concentrically.

Figure 3:
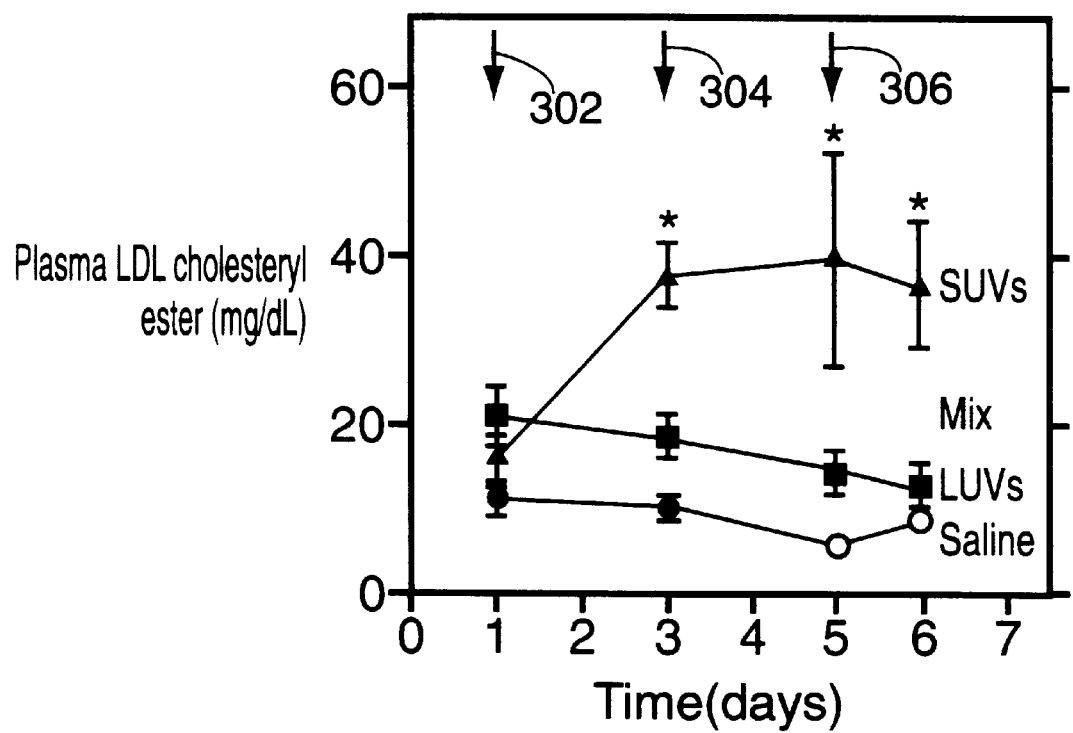
FIGS. 3 and 4 illustrate plasma LDL cholesteryl ester concentrations in response to injections of LUVs, SUVs or saline over time in one variant.
Figure 4:
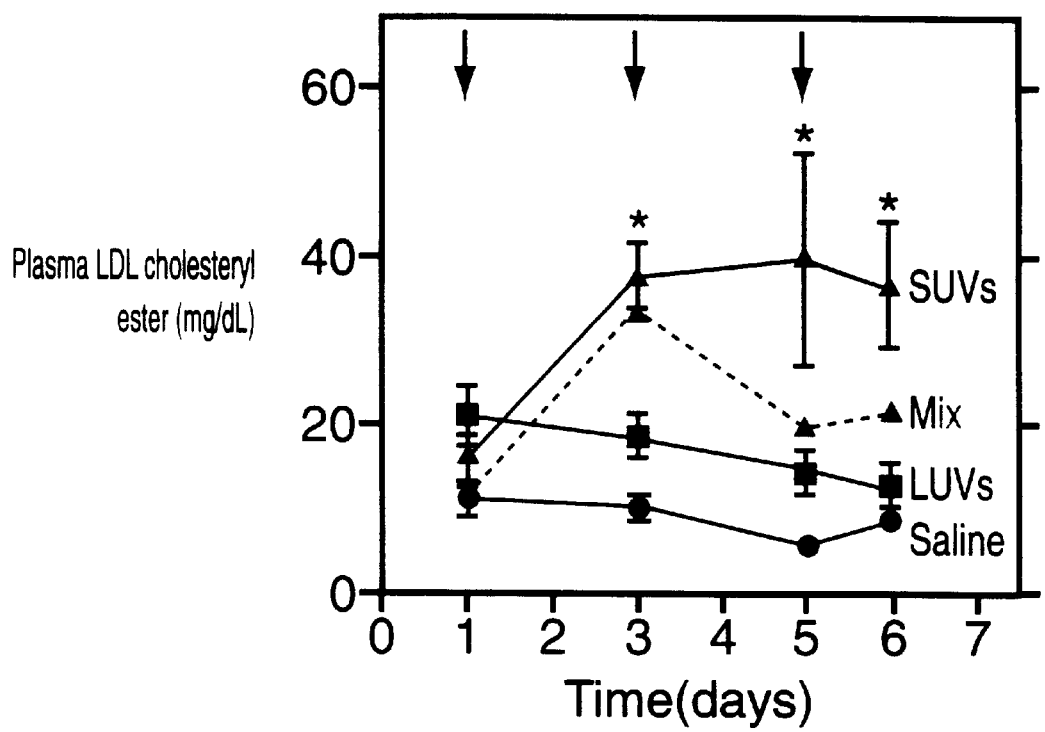

FIGS. 3 and 4 illustrate plasma LDL cholesteryl ester concentrations in response to injections of LUVs, SUVs or saline over time. Rabbits were intravenously injected on days 1, 3 and 5 as indicated by arrows 302, 304, and 306 respectively, with a bolus of 300 mg of phosphatidylcholine per kg of body weight or a matched volume of saline. The phosphatidylcholine was pharmaceutical grade egg PC, in the form of either large unilamellar vesicles (LUVs) having diameters of approximately 100 NM (preferably ≅120 NM) prepared by extrusion (LUVs were measured at about 120 NM (123±35 NM and the extrusion membrane had pores of about 100 NM in diameter) or small unilamellar vesicles with diameters of approximately 30 NM (preferably 35 NM) prepared by sonication. (SUVs were measured in the range of 34±30 NM.) Blood was drawn just before each injection and on the sixth day at sacrifice. Plasma LDL cholesteryl ester concentrations were determined by a gel filtration assay of the plasma with an in-line enzymatic assay for cholesteryl ester. Means ±SEMs are shown in FIG. 3. Animals infused with SUVs showed significantly higher plasma concentrations of LDL cholesteryl ester at days 3, 5, and 6 compared to either LUV-infused or saline infused animals. FIGS. 2–8, 10–15, 24 and 28 illustrate data from the same experiment in which injections were made on days 1, 3, and 5 and then livers were taken. Gel filtration was done of plasma to measure lipid contents of individual lipoprotein classes. FIG. 2 illustrates a table of hepatic mRNA content (pg/$\mu$g) for CETP, HMG-CoA R (hydroxy methylglutaryl coenzyme A reductase), LDL receptors, and cholesterol 7 alpha-hydroxylase; and LDL ChE (low density lipoprotein cholesteryl ester) for the rabbits given saline (HEPES buffered saline) (rabbits 1–4), LUVs (rabbits 5–8), and SUVs (rabbits 10–12) for the experiment described for FIGS. 3 and 4. Rabbit 13 is the "Mix" rabbit.

FIG. 4 shows an animal labeled as mix. "Mix" refers to a single animal that received SUVs on day 1, 3 and 5, but also one injection of LUVs on day 3. Before this injection of LUVs, the plasma concentration of LDL cholesteryl ester rose, but after the injection of LUVs, the LDL concentration fell, despite continued injections of SUVs.

Figure 5:
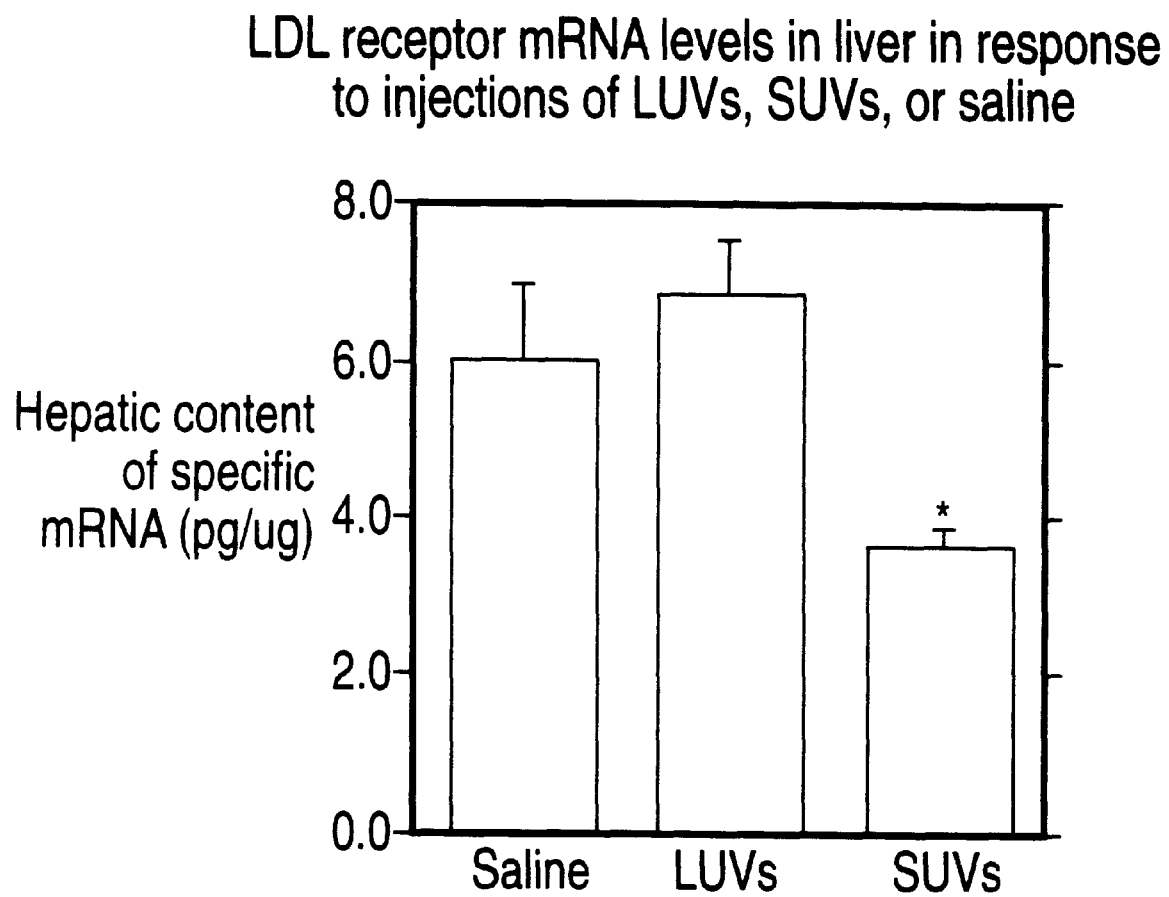
FIG. 5 illustrates LDL receptor mRNA levels in liver in response to injections of LUVs, SUVs or saline over time.

FIG. 5 illustrates LDL receptor mRNA levels in liver in response to injections of LUVs, SUVs or saline over time. The rabbits described above were sacrificed at day 6, and samples of liver were snap-frozen in liquid nitrogen. mRNA was extracted, and rabbit mRNA for the LDL receptor was quantified by an internal standard/RNase protection assay (Rea T. J. et al. J. Lipid Research 34:1901–1910, 1993 and Pape M. E., Genet. Anal. 8:206–312, 1991). Means ±SEMs are shown in FIG. 5. Animals infused with SUVs showed significant suppression of hepatic LDL receptor mRNA compared to LUV-infused or saline-infused animals. Suppression of hepatic LDL receptor mRNA reflects parenchymal cell overload with sterol, and is a potentially harmful alteration from normal hepatic cholesterol homeostasis. In contrast, LUV-infused animals showed the highest levels of hepatic LDL receptor mRNA, though the increase above that seen in the saline-infused animals did not reach statistical significance. The liver from the "Mix" animal described above showed a value of 5.28 pg LDL receptor mRNA/microgram which is closer to the average value in the saline group than in the SUV group. Thus, LDL receptor mRNA was stimulated by the single injection of LUVs despite repeated injections of SUVs.

Figure 6:
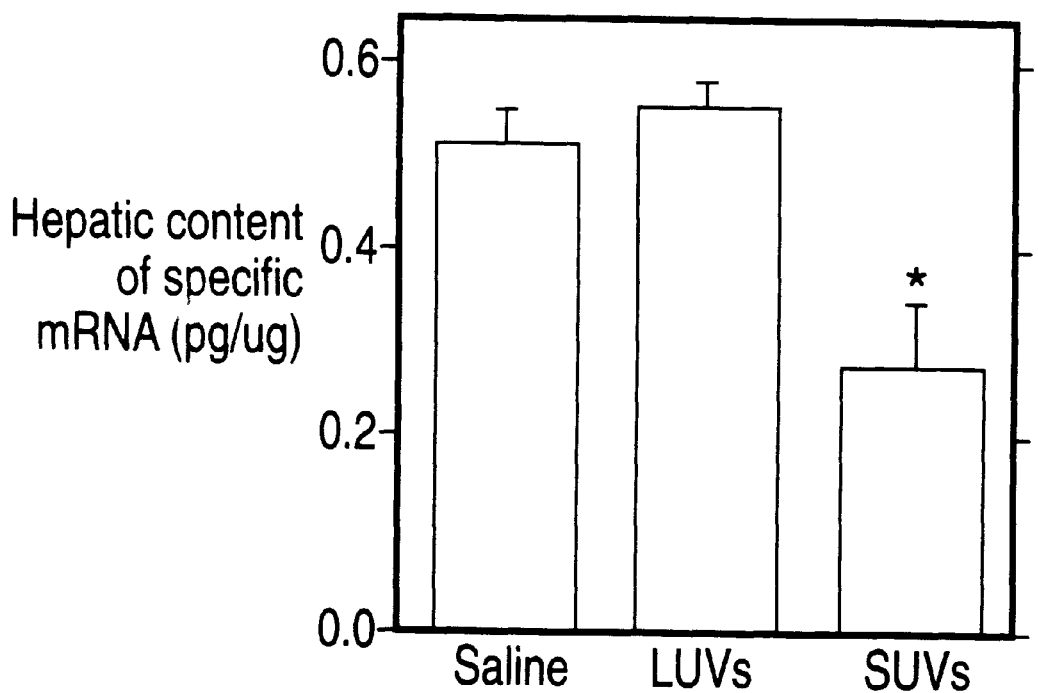
FIG. 6 illustrates HMG-CoA reductase mRNA levels in liver in response to injection of LUVs, SUVs, or saline.

FIG. 6 illustrates HMG-CoA reductase mRNA levels in liver in response to injections of LUVs, SUVs, or saline. The experimental details are those as referenced above. Animals infused with SUVs showed significant suppression of hepatic HMG-CoA reductase mRNA compared to LUV-infused or saline infused animals. Suppression of hepatic HMG-CoA reductase mRNA reflects parenchymal cell overload with sterol, which can be a potentially harmful alteration from normal hepatic cholesterol homeostasis. In contrast, LUV-infused animals showed the highest levels of hepatic HMG-CoA reductase mRNA, though the increase above that seen in the saline-infused animals did not reach statistical significance.

The "mix" animal showed a value of 0.50 pg HMG-CoA reductase mRNA/microgram, which is essentially identical to the average value in the saline group (0.51) and substantially higher than the value in the SUV group (0.27). Thus, HMG-CoA reductase mRNA was stimulated to its normal value by the single injection of LUVs, despite repeated injections of SUVs.

Figure 7:
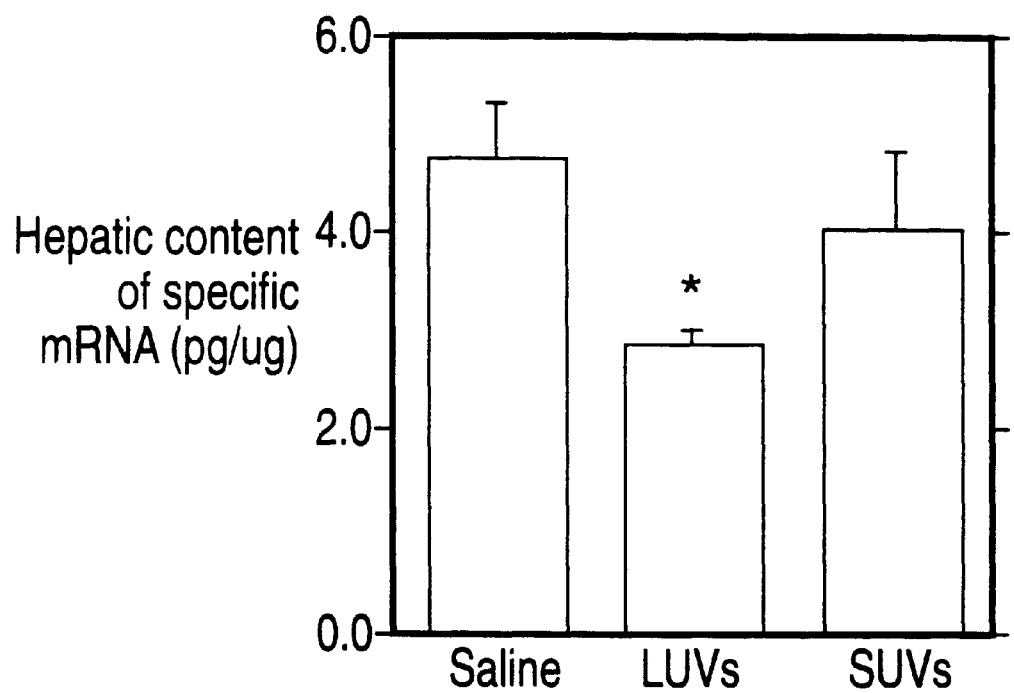
FIG. 7 Illustrates cholesteryl ester transfer protein mRNA levels in liver in response to injection of LUVs, SUVs, or saline.

FIG. 7 illustrates cholesteryl ester transfer protein mRNA levels in liver in response to injection of LUVs, SUVs, or saline. The experimental details are those as referenced above.

Animals infused with LUVs showed significant suppression of hepatic CETP mRNA compared to SUV infused or saline infused animals. Suppression of CETP mRNA produce changes in the plasma lipoprotein profile usually associated with reduced risk of atherosclerosis. The "mix" animal showed a value of 3.18 pg CETP mRNA/microgram, which is closer to the average value in the LUV group than in the SUV or saline groups. Thus, CETP mRNA was suppressed by the single injection of LUV's despite repeated injections of SUVs.

Figure 8:
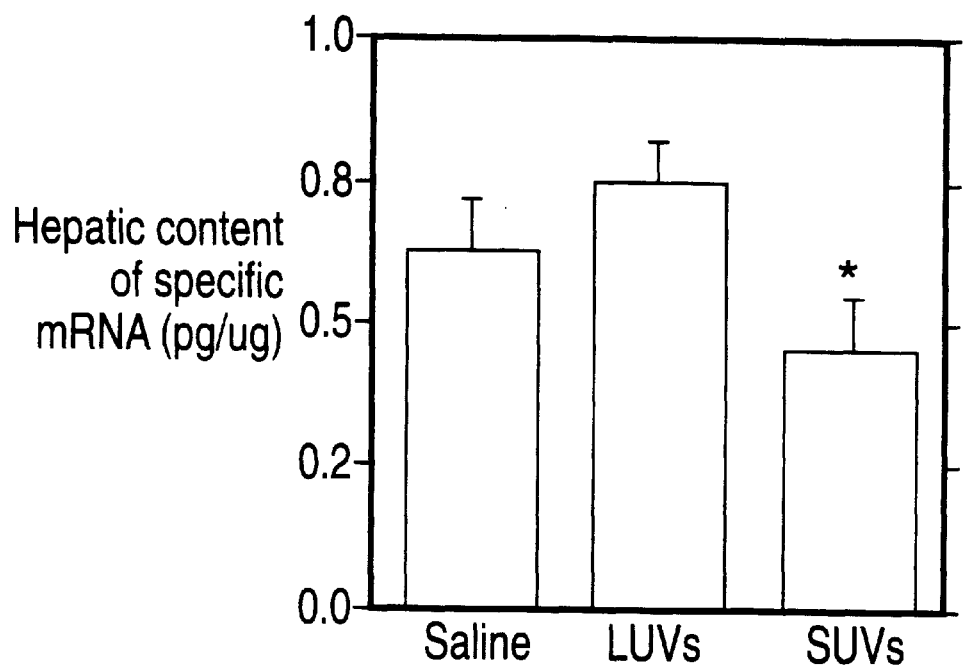
FIG. 8 illustrates 7-alpha hydroxylase mRNA levels in liver in response to injections of LUVs, SUVs, or saline.

FIG. 8 illustrates cholesterol 7-alpha hydroxylase mRNA levels in liver in response to injections of LUVs, SUVs, or saline. The experimental details are those as reference above. Animals infused with SUVs showed suppression of hepatic 7-alpha hydroxylase mRNA compared to LUV infused or saline infused animals. Suppression of 7-alpha hydroxylase can be a potentially harmful alteration from normal hepatic homeostasis. In contrast, LUV-infused animals showed the highest levels of hepatic 7-alpha hydroxylase mRNA, though the increase above that seen in the saline infused animals did not reach statistical significance. The "mix" animal showed a value of 0.51 pg 7-alpha hydroxylase mRNA/microgram, which is higher than the average value in the SUV group. Thus, 7-alpha-hydroxylase mRNA was stimulated by the single injection of LUVs, despite repeated injections of SUVs.

Figure 10:
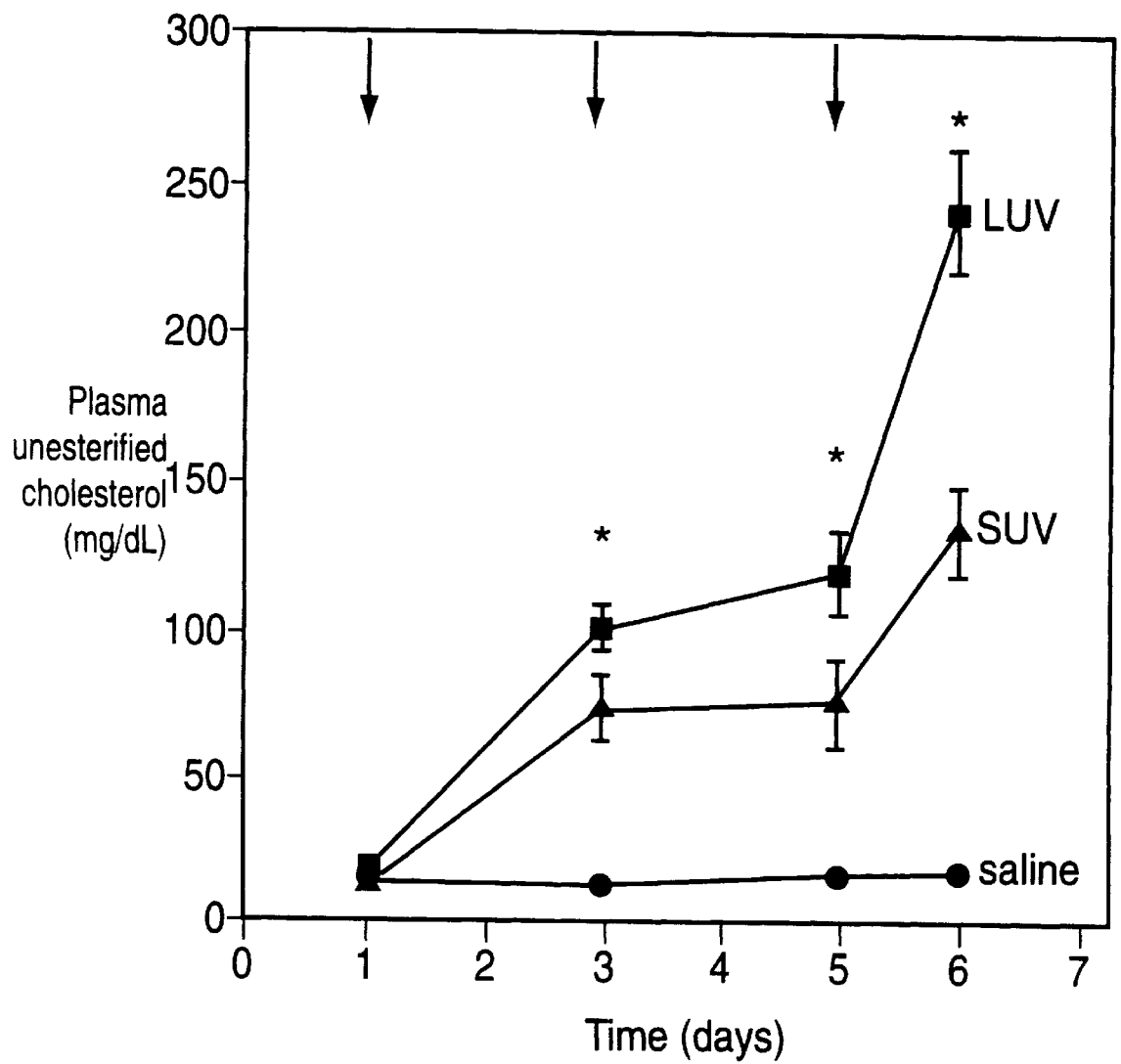
FIG. 10 illustrates plasma LDL unesterified cholesterol concentrations in response to injections of LUVs, SUVs or saline over time.

FIG. 10 illustrates unesterified cholesterol concentrations in whole plasma in response to injections of LUVs, SUVs, or saline over time. The experimental details are those as referenced above. As indicated by this figure, LUVs and SUVs significantly raised the plasma concentrations of unesterfied cholesterol indicating mobilization of tissue stores. The LUVs raised the concentration of unesterifed cholesterol more than did the SUVs.

Figure 11:
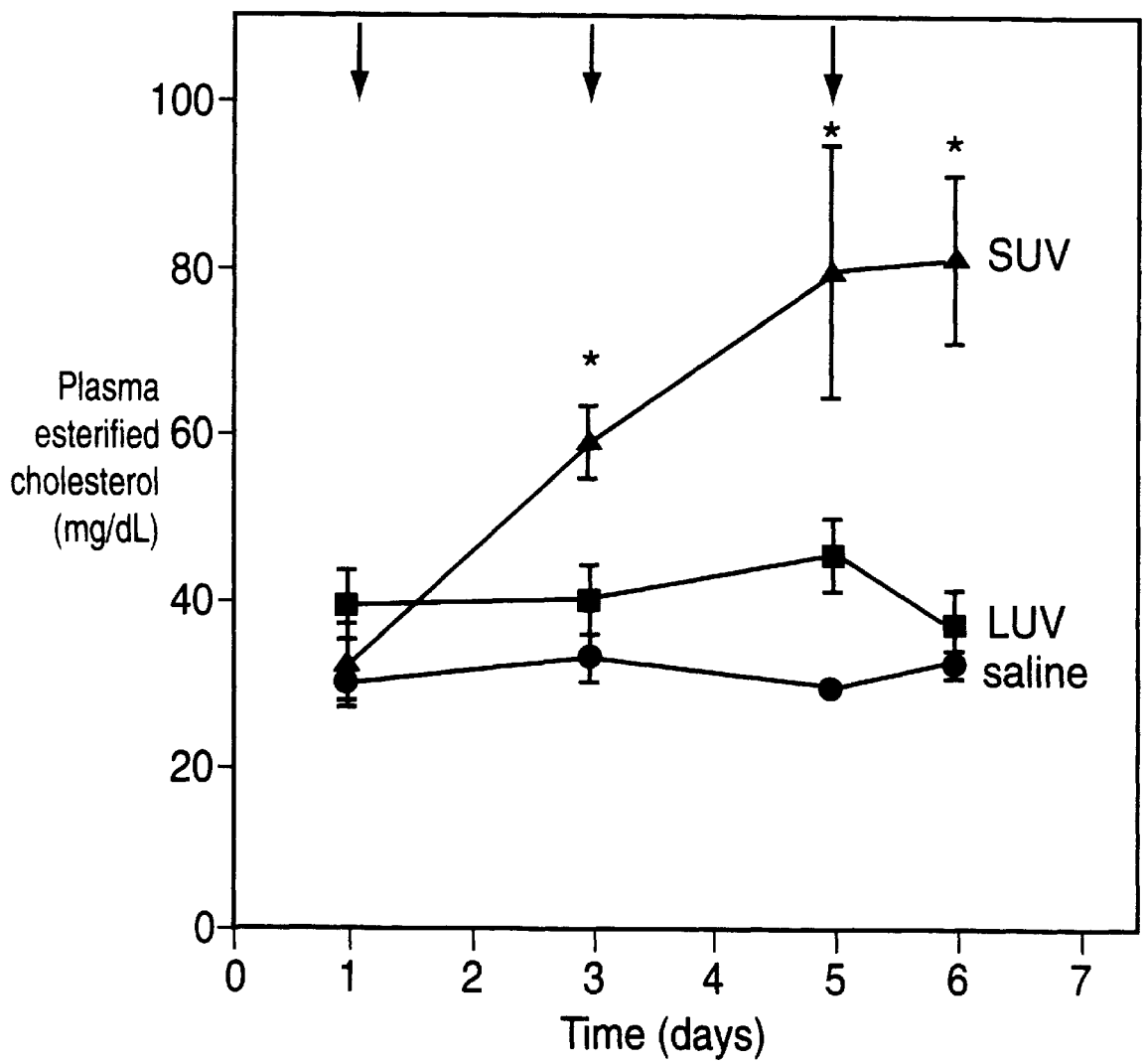
FIG. 11 illustrates plasma LDL esterified cholesterol concentrations in response to injections of LUVs, SUVs or saline over time.
Figure 12:
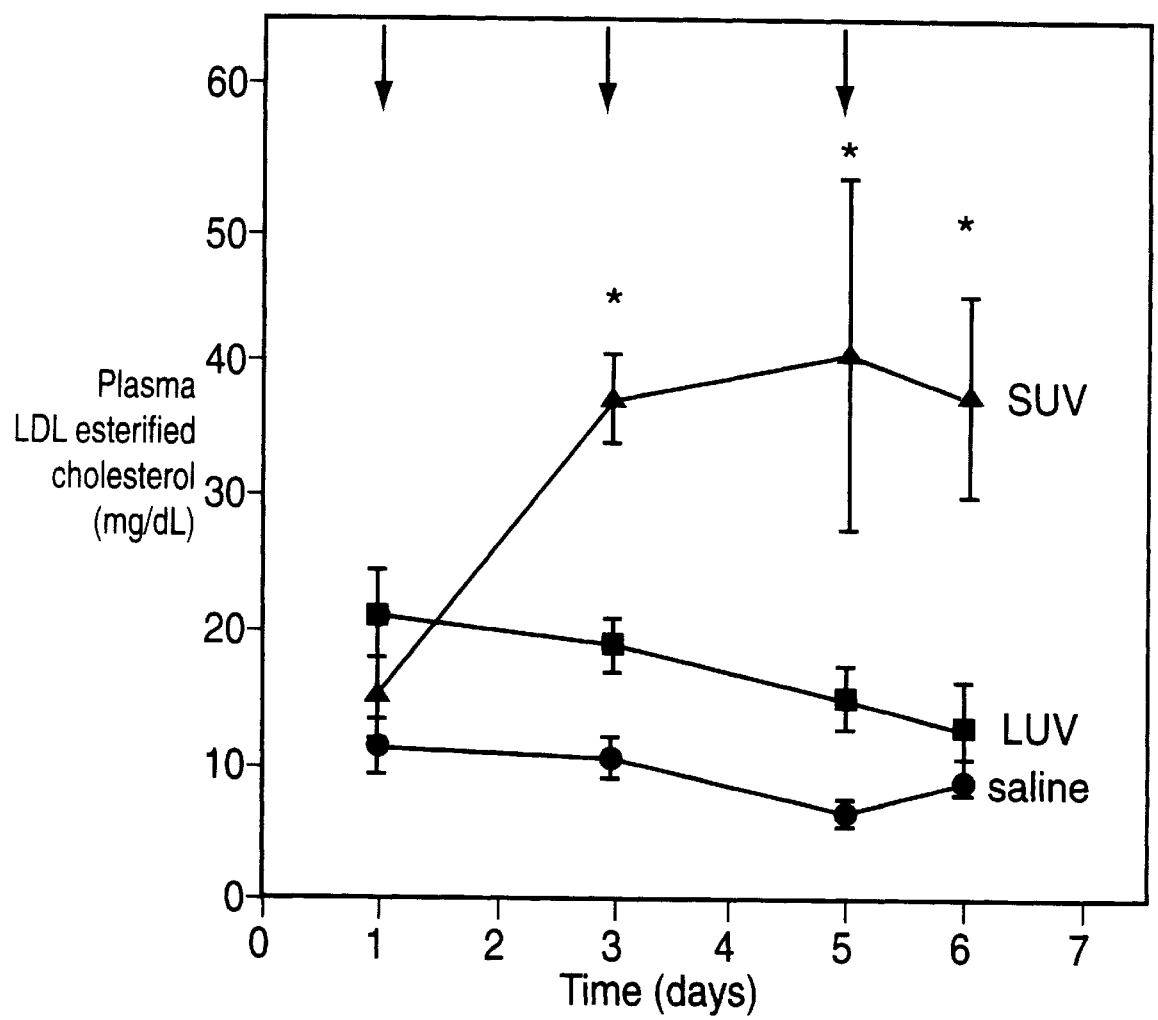
FIG. 12 illustrates LDL esterified cholesterol concentrations in response to injections of LUVs, SUVs or saline.

FIG. 11 illustrates esterified cholesterol concentrations in whole plasma in response to injections of LUVs, SUVs or saline over time. The experimental details are those as referenced above. SUVs raised the plasma concentrations of cholesteryl ester on days 3, 5, and 6. FIG. 12 duplicates the information contained in FIG. 3.

Figure 13:
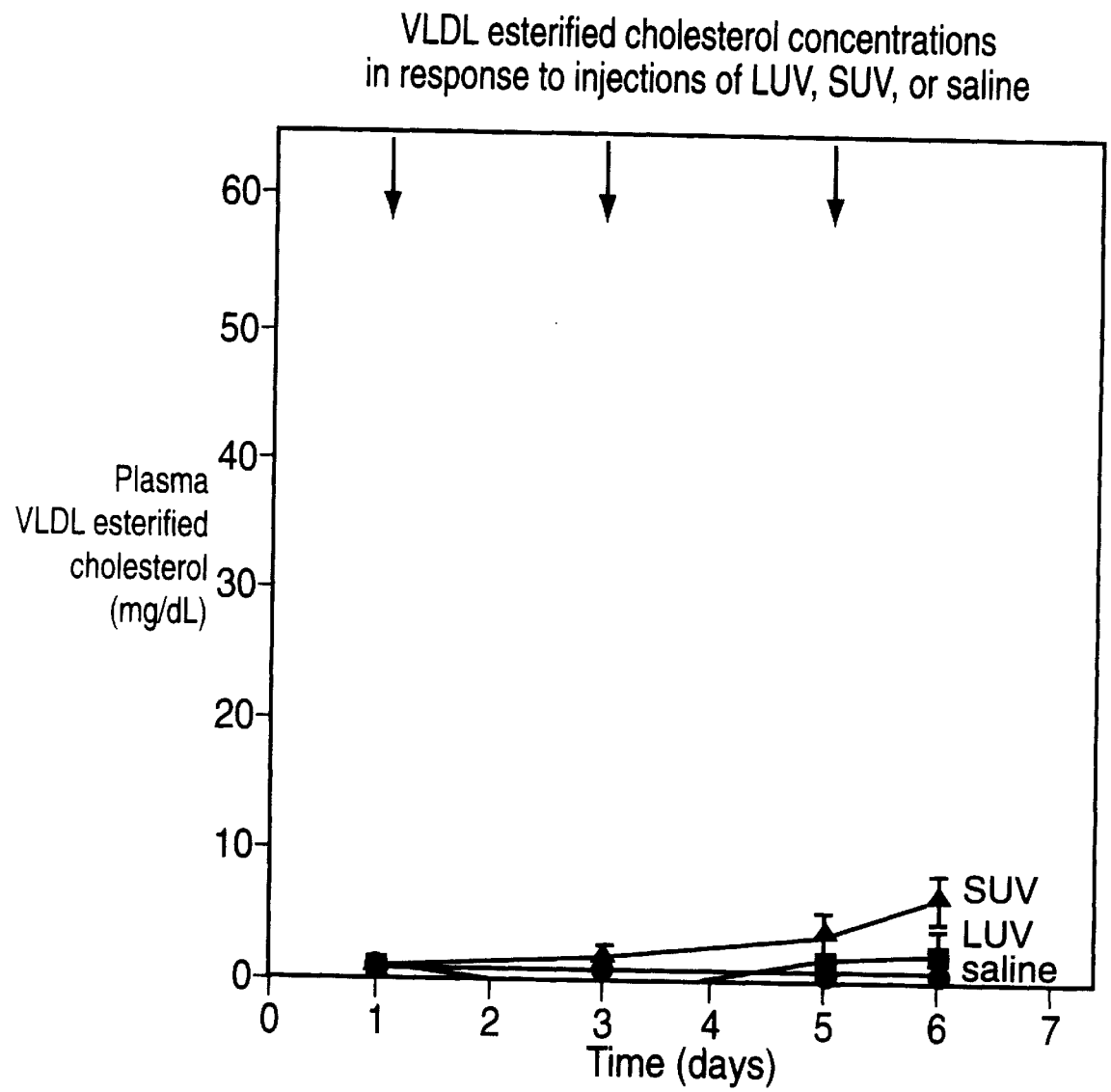
FIG. 13 illustrates plasma VLDL esterified cholesterol concentrations in response to injections of LUVs, SUVs or saline.

FIG. 13 illustrates plasma VLDL esterified cholesterol concentrations in response to injections of LUVs, SUVs, or saline. SUVs increased the plasma concentration of VLDL cholesteryl ester over that seen in the saline of LUV treated groups. The "mix" animal showed a plasma VLDL cholesteryl ester concentration at day 6 of 2.4 mg/dl, which is lower than the average value in the SUV group. The experimental details are those as referenced above.

Figure 14:
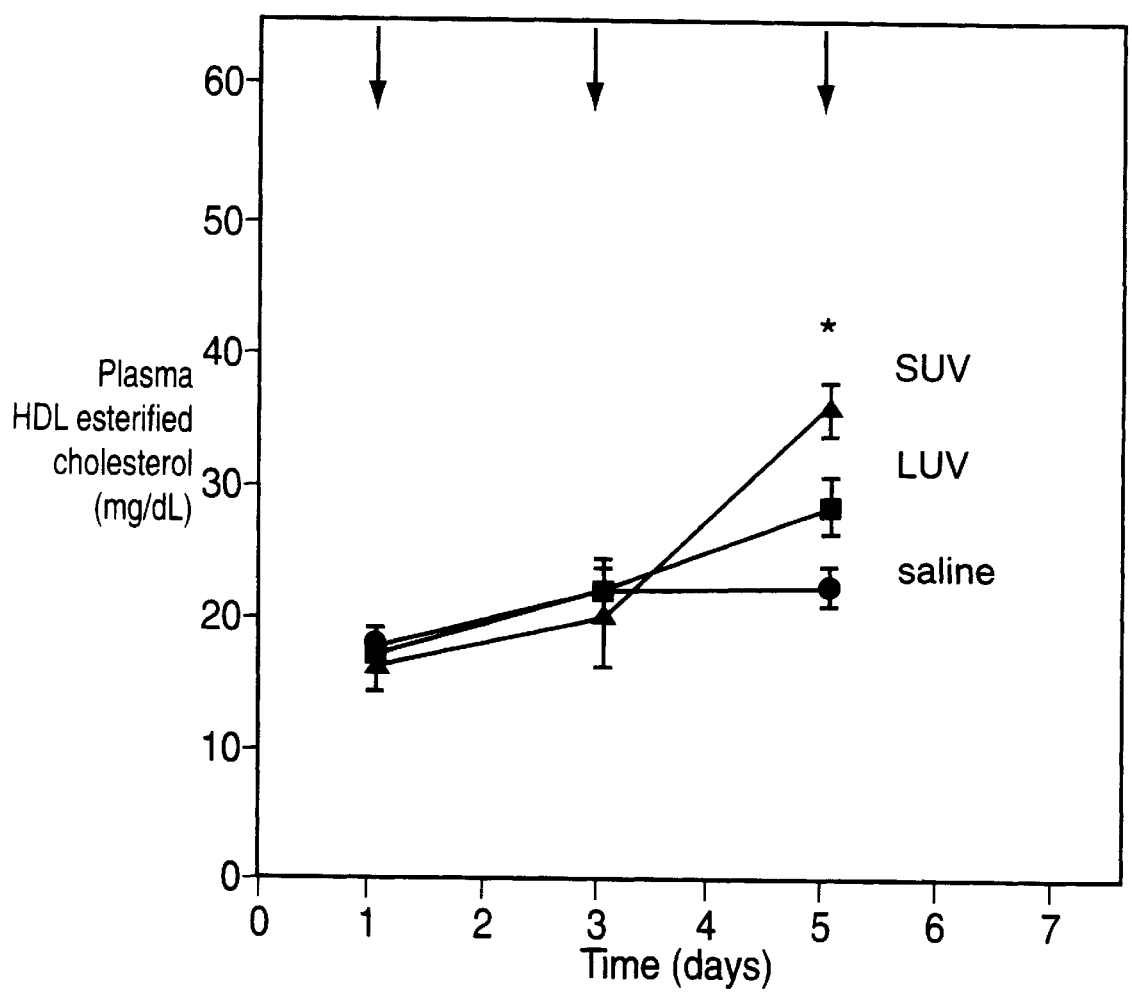
FIGS. 14 and 15 illustrate HDL esterified cholesterol concentrations in response to injections of LUVs, SUVs or saline.
Figure 15:
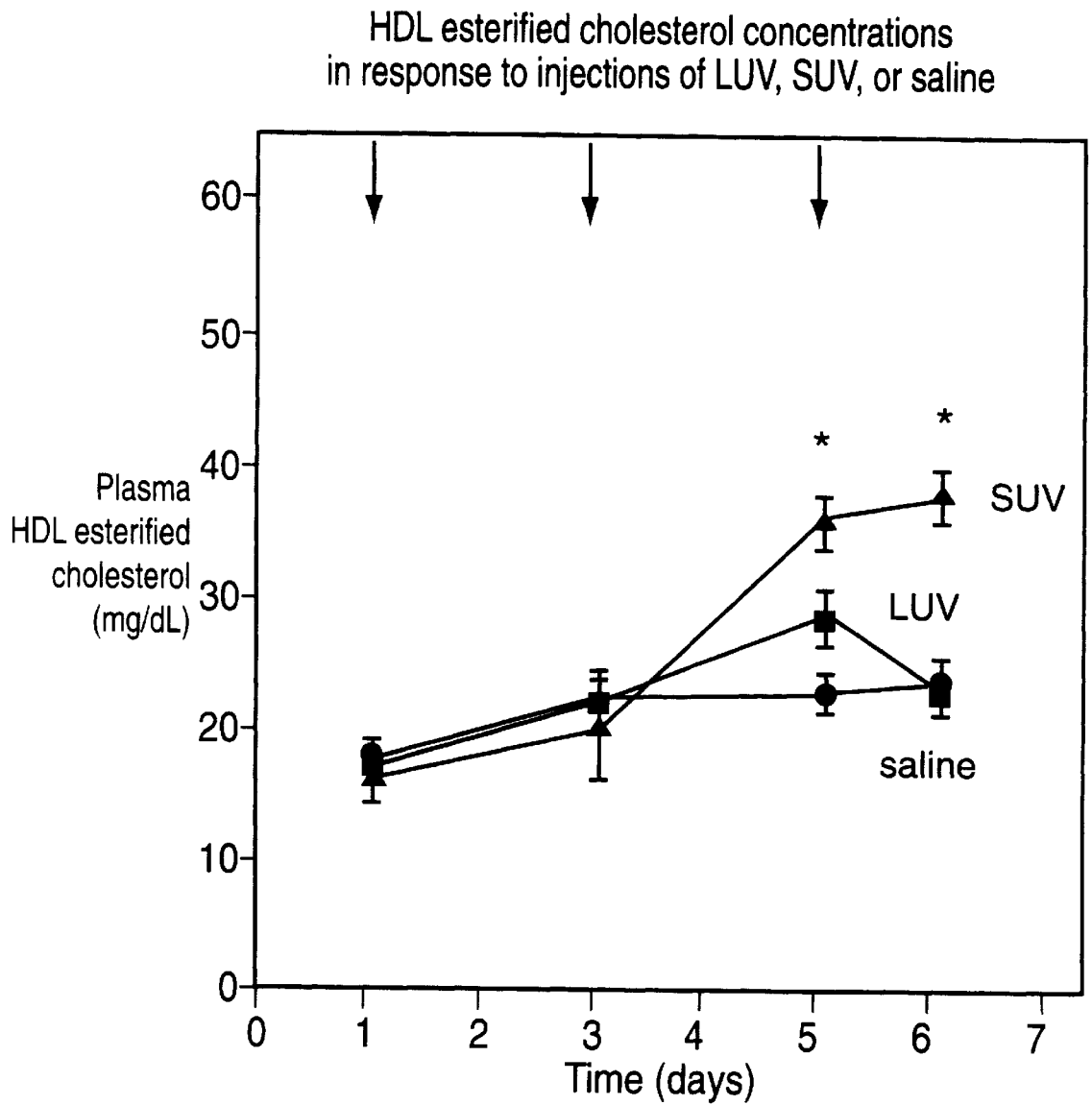

FIGS. 14 and 15 illustrate HDL esterified cholesterol concentrations in response to injections of LUVs, SUVs, or saline. The experimental details are those as referenced above as in FIG. 2. Suitable phospholipid can be obtained from Avanti Polar Lipids, Nippon Oil and Fat in Japan and Princeton Lipids, as well as other suppliers. LUVs are made through an extruder that is commercially available. SUVs caused a small but statistically significant rise in HDL cholesteryl ester concentrations on days five and six.

Figure 16:
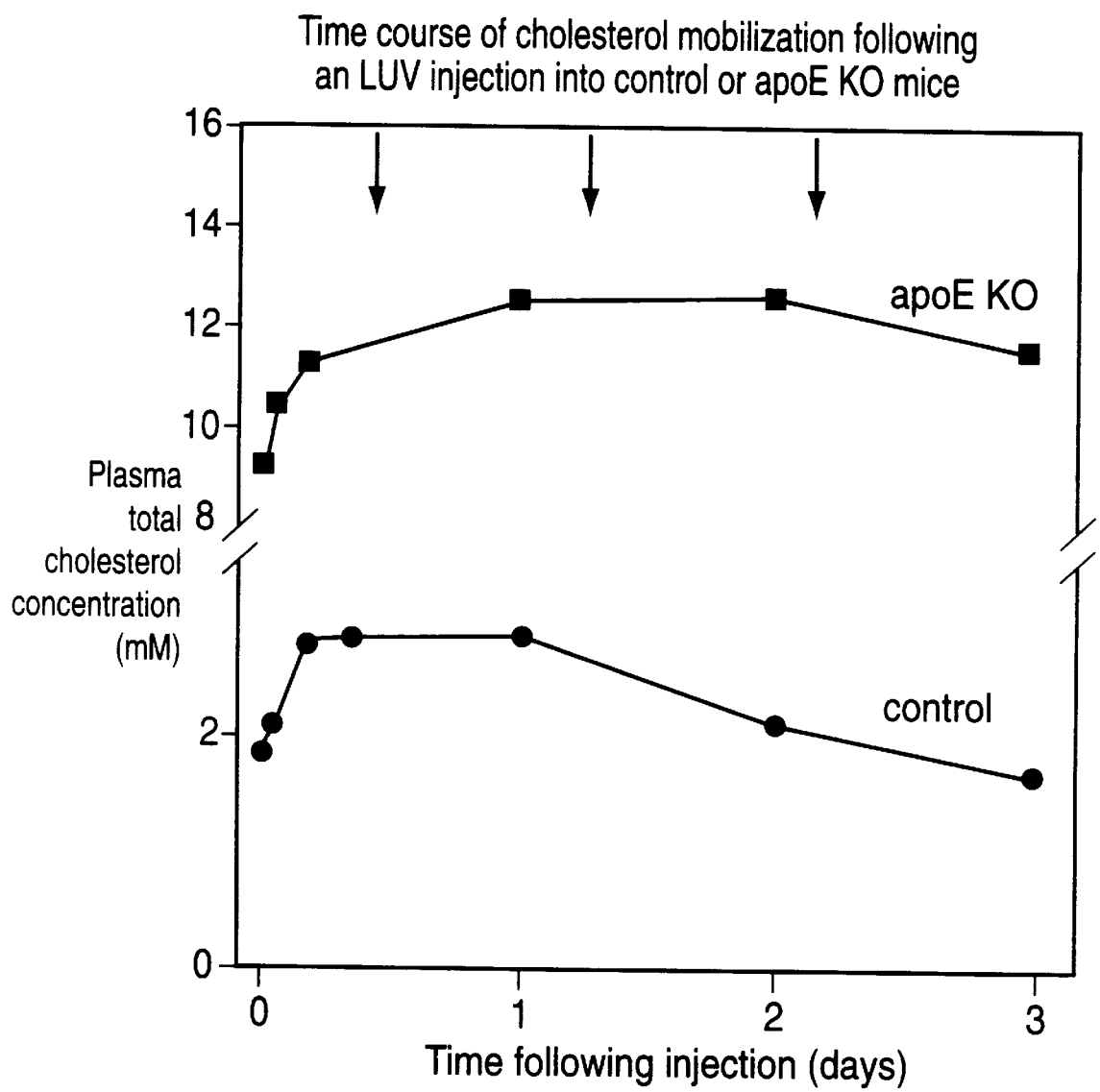
FIG. 16 illustrates the time course of cholesterol mobilization following an LUV injection into control or apoE KO mice.

FIG. 16 illustrates the time course of cholesterol mobilization following an LUV injection into control or apoE KO (knock-out) mice commercially available from Jackson Laboratories, in Bar Harbor, Me. Control (C57/BL6) and apolipoprotein E knock-out mice were injected at time zero with a single bolus of 300 mg LUV phospholipid/kg body weight. The LUVs contained a tracer amount of labeled cholesteryl hexadecylether, which remains on the liposomes after injection into a mouse. Displayed data are for concentrations of total cholesterol, i.e. esterified plus unesterifed, in whole plasma. The rise in both sets of animals indicated that LUVs mobilize cholesterol into the plasma, even in the presence of a severe genetic hyperlipidemia.

Figure 17:
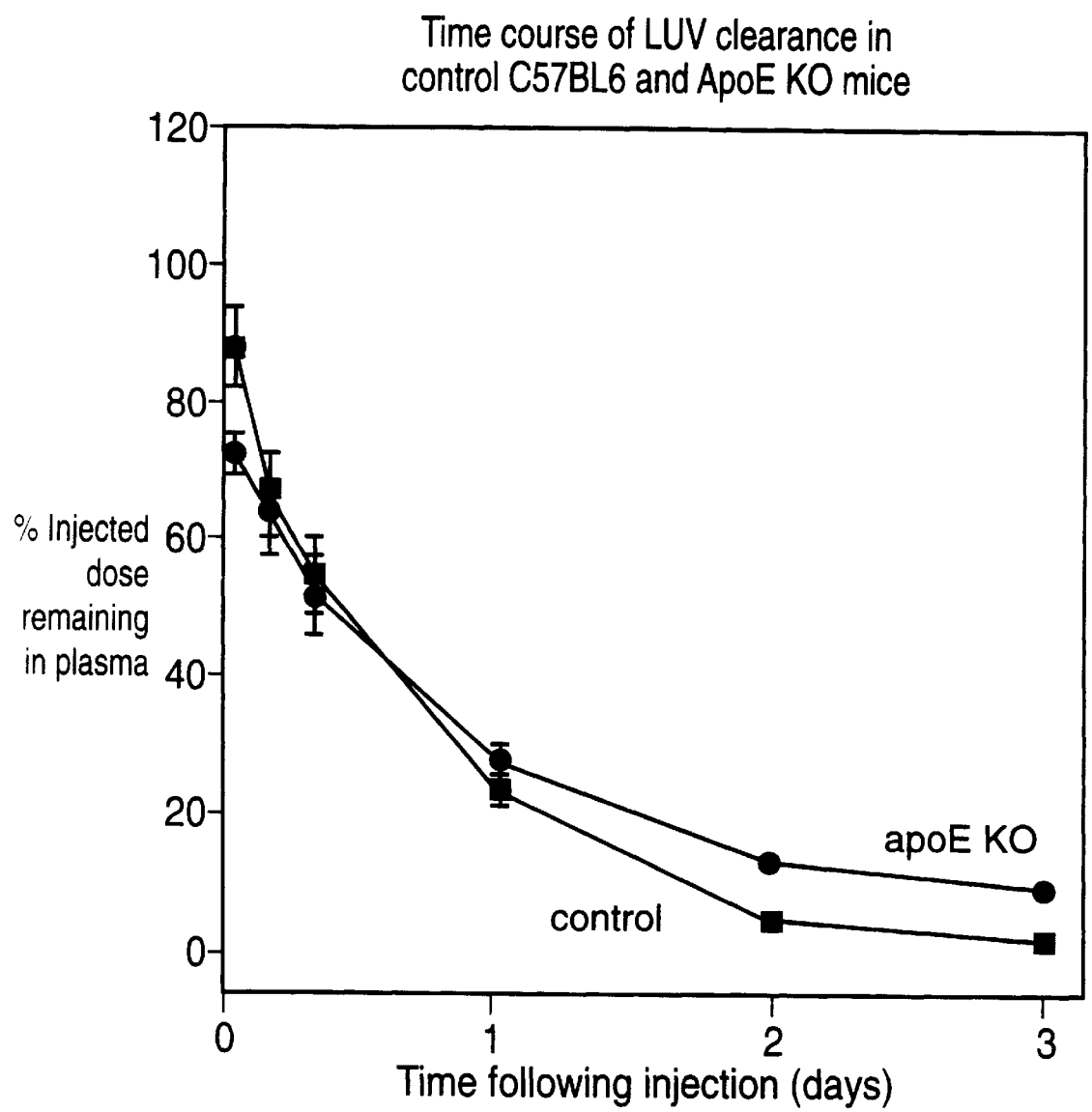
FIG. 17 illustrates the time course of LUV clearance in control mice and apoE mice.

FIG. 17 illustrates the time course of LUV clearance in control mice and apoE mice. The experimental details are as described in FIG. 16. The clearance of LUVs from the plasma is unimpaired in the apoE knock-out mice, indicating mobilization (FIG. 16) and disposal (FIG. 17) of cholesterol even in the presence of a severe genetic hyperlipidemia. This indicates the usefulness of this preparation in hyperlipidemias.

FIG. 18 illustrates exemplary applications for the compositions and methods of the present invention in humans. The therapeutic targets of the compositions and methods presented herein are lipid-rich, rupture prone plaques, critical stenosis, post-angioplasty re-stenosis, atherosclerosis in general, and any membrane, cell, tissue, organ, and extra-cellular region and/or structure, in which compositional and/or functional modifications would be advantageous.

Figure 19:
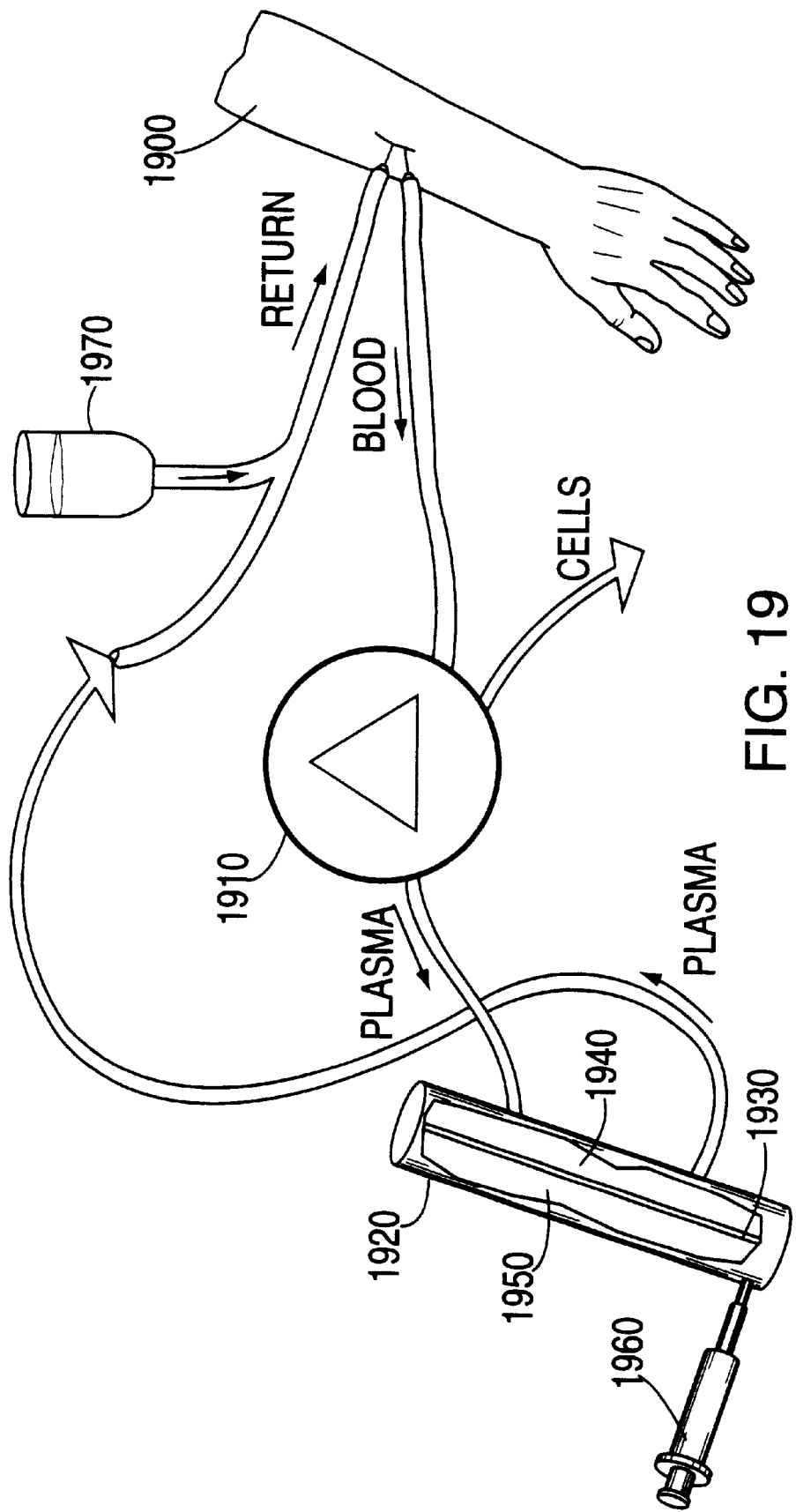
FIG. 19 illustrates a perspective view of an improved hemodialysis system of the present invention and improved method of hemodialysis.

FIG. 19 illustrates a perspective view of an improved hemodialysis system of the present invention and improved method of hemodialysis. Blood is taken from a site for circulatory access (shown here as arm 1900) and transported into a cell-plasma separator 1910. The plasma is then transported to a dialysis chamber 1920 and is divided into at least two compartments that are separated by a semi-permeable membrane 1930. One side of the membrane 1930 is the patient's plasma 1940 and on the other side is the dialysate 1950. Selected molecules exchange across the membrane 1930 depending on the characteristics of the membrane (charge, pore size, etc.). The device 1960 comprises a device for adding lipid acceptors to the dialysate and for sampling the dialysate to allow assays of cholesterol, phospholipid, and other components, such as acceptors, specific lipoproteins, specific components, and to monitor treatment. Extraction of plasma cholesterol or other extractable material comprises several possibilities: 1) acceptors are disposed in the dialysate that do not cross membrane 1930 into plasma; 2) the acceptors do cross membrane 1930 and are either left in the plasma and returned to the patient or are separated from plasma before it is returned to the patient; and/or 3) immobilized acceptors on a sheet (such as membrane 1930 itself), on beads, and/or on the walls of the chamber 1920. Plasma thus treated is returned to the patient, usually after having being re-mixed with the blood cells. As noted, cholesterol acceptors can be added at any stage, as an example, a device 1970 comprises acceptors and for adding acceptors to plasma shortly before its return into the patient is also illustrated in FIG. 19. It is further understood that contaminating cellular material, such as platelets, in the plasma will also become cholesterol depleted in endogenous lipids and enriched in phospholipid. It is further understood that all acceptors mentioned throughout this application may accept molecules in addition to cholesterol and may donate material as well.

The cellular concentrate from the cell-plasma separator 1910 can then be treated in any of several ways before being returned to the patient: 1) returned to the patient with no further treatment (this includes being mixed with plasma that has been treated as above); 2) transferred to a second dialysis chamber (not shown) in which the dialysate contains cholesterol acceptors to lipid deplete the cells of endogenous lipids, such as cholesterol, before their return to the patient; 3) mixed with a suspension or solution of lipid acceptors to lipid deplete the cells of endogenous lipids, then either returned to the patient with the acceptors or option 1) and option 2) above can be performed with all cell types together, or after further separation into specific cell types (for example, purified platelets could be lipid depleted of endogenous lipids, such as cholesterol, and enriched in liposomal lipids). Options 2) and 3) can be performed with periodic assays of cellular cholesterol, phospholipid, fluidity, viscosity, fragility, cell composition and/or cell function. Devices 1960, 1970 include an apparatus that allows for the periodic sampling of cells during treatment. As with plasma, lipid acceptors can be added at any stage of the treatment. All fluids, e.g. plasma and concentrated cells, are moved by gravity, mechanically, by manual manipulation (a syringe), or with pumps as needed. Of course, it is understood that blood can be drawn for processing from any appropriate part of the body.

Figure 20:
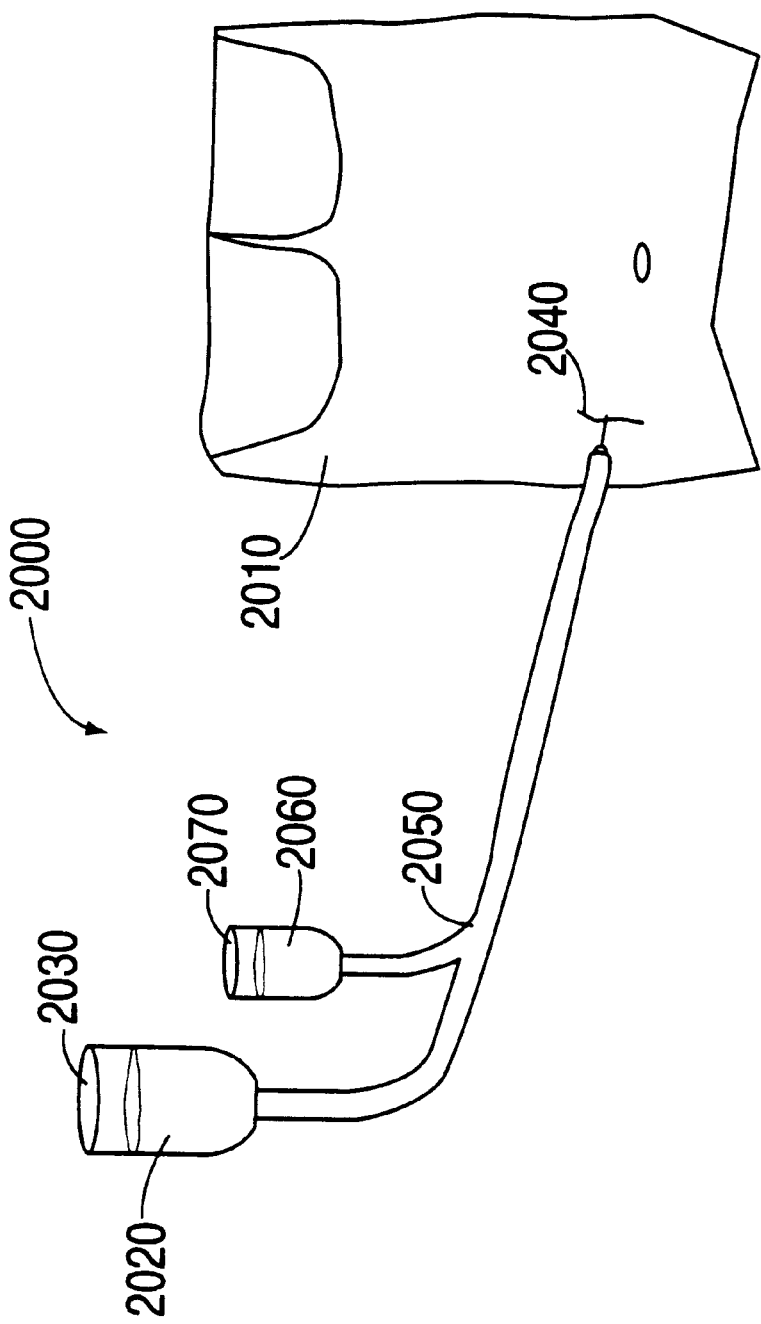
FIG. 20 illustrates a perspective view of an improved peritoneal dialysis system 2000 and method of peritoneal dialysis.

FIG. 20 illustrates a perspective view of an improved peritoneal dialysis system 2000 and method of peritoneal dialysis. Patient's abdomen 2010 (FIGS. 20–21) receives peritoneal dialysate 2020 stored in container 2030 into the peritoneal cavity through incision 2040 by way of channel 2050. Lipid acceptors and/or cholesterol acceptors 2060 are optionally disposed in container 2070. In another variant, lipid acceptors are added to dialysate 2020; added to container 2030 in concentrated form shortly before infusion; added as shown to the stream of fluid entering the peritoneal cavity; or infused by a separate portal of entry into the patient by any effective route. Throughout this application, it is understood that all acceptors may accept molecules in addition to cholesterol and may donate material such as phospholipids and antioxidants.

Figure 21:
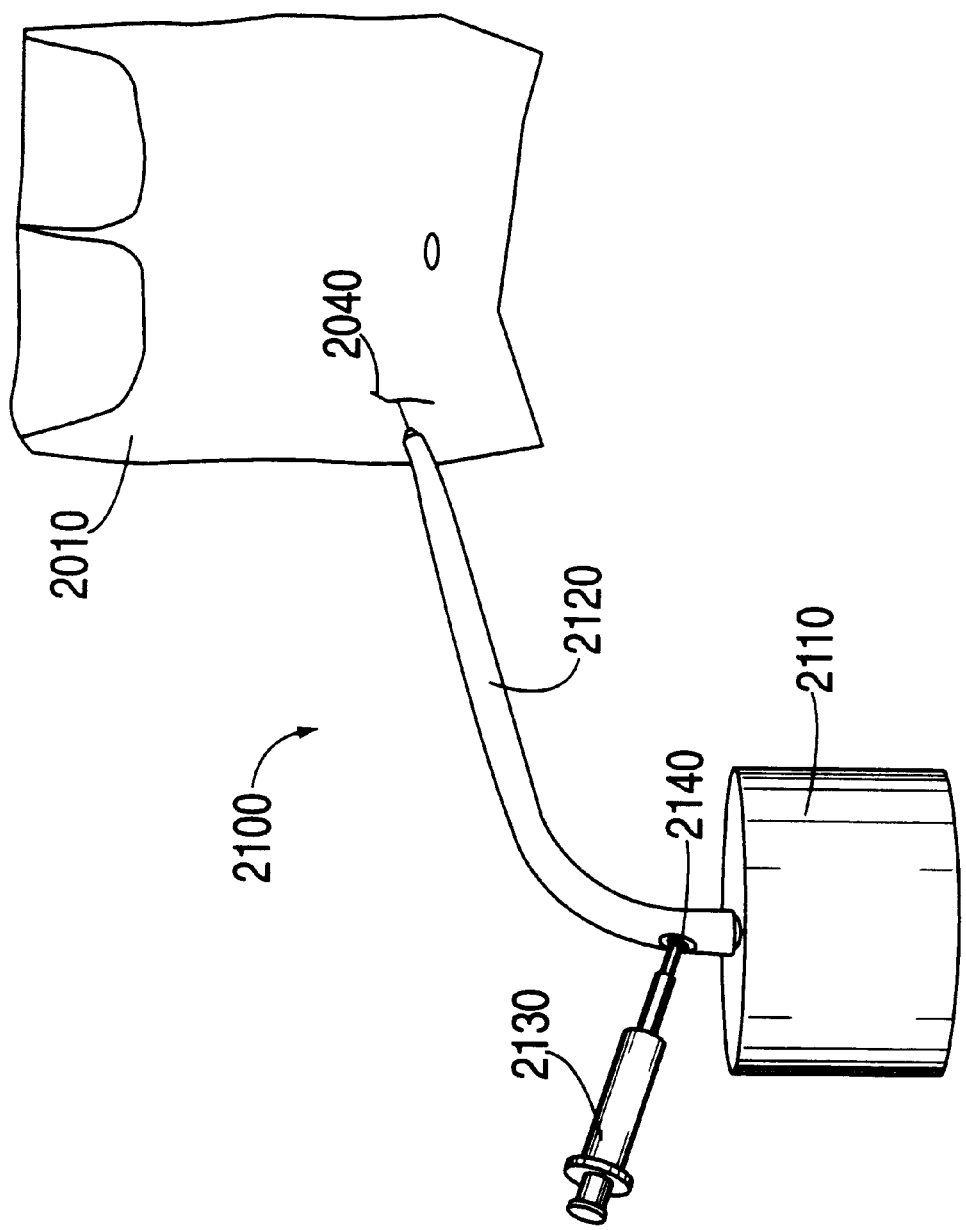
FIG. 21 illustrates a perspective view of a variant of an improved peritoneal dialysis system with assaying means 2100 and method of peritoneal dialysis and analysis of spent fluid.

FIG. 21 illustrates a perspective view of a variant of an improved peritoneal dialysis system with assaying means 2100 and method of peritoneal dialysis and analysis of spent fluid. Container 2110 accepts spent fluid from abdomen 2010 by way of channel 2120. The device 2110 provides access to diagnostic samples of spent dialysate to allow for assay of cholesterol, phospholipid, and other parameters as described herein showing the efficacy of the treatments described. Optionally, assay syringe 2130 is inserted by way of access portal 2140 into channel or tube 2120, or into container 2110, and optional pumps (not shown) are used to move the various fluids to appropriate locations for assay thereof.

Figure 22:
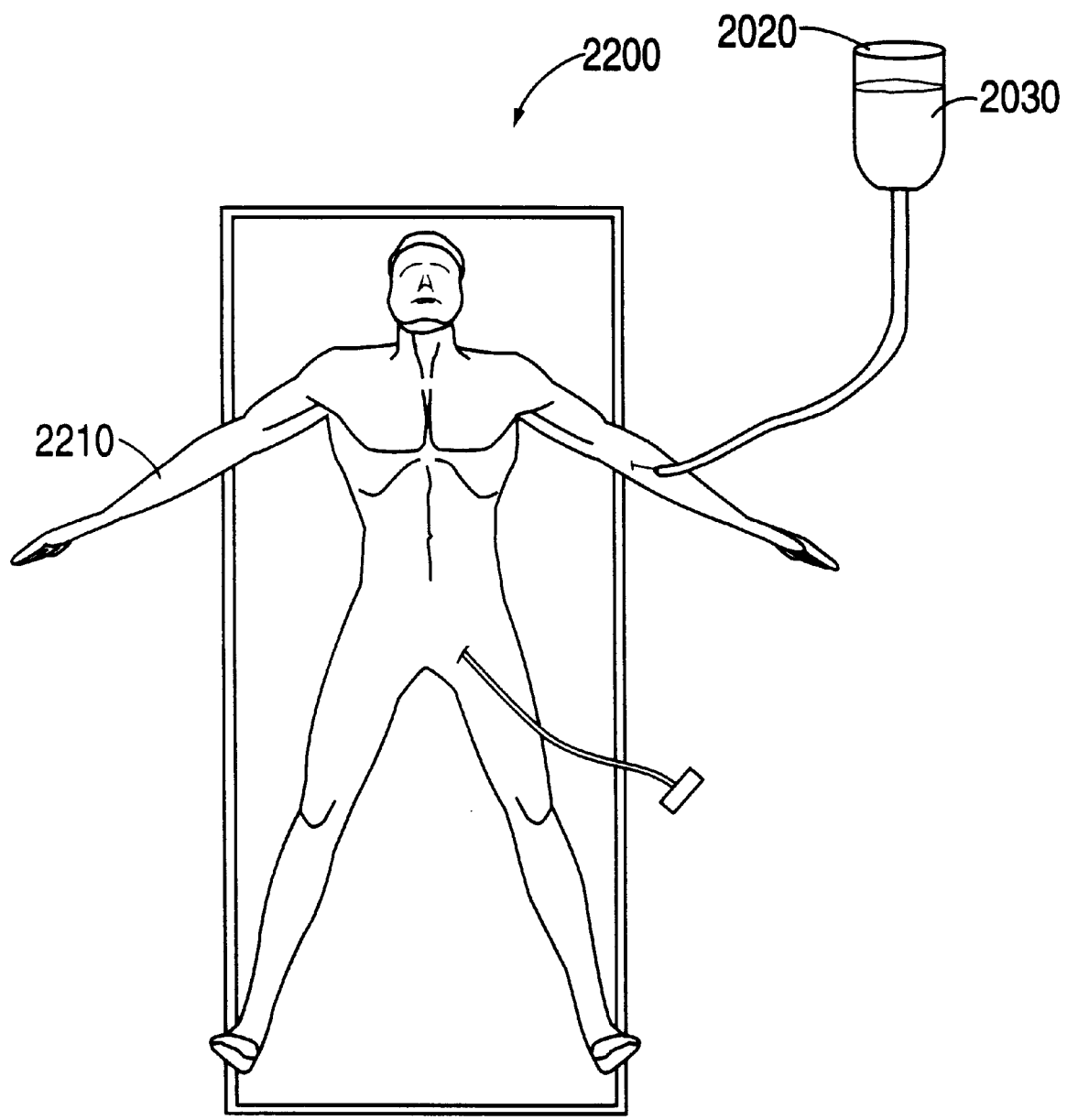
FIG. 22 illustrates a perspective view of an improved cardiac catheterization and/or angioplasty system 2200 and method of cardiac catheterization and/or angioplasty.

FIG. 22 illustrates a perspective view of an improved cardiac catheterization and/or angioplasty system 2200 and method of cardiac catheterization and/or angioplasty. Patient 2210 undergoes cardiac catherization and/or angioplasty. The patient intravenously receives effective doses of lipid acceptors or cholesterol acceptors 2230 co-administered with said treatment(s) from container 2220. Intraarterial access of a catheter for coronary angiography and/or angioplasty allows for ready co-administration of cholesterol acceptors and administration of diagnostic agents such as cholinergic agents, to assess vascular function.

Figure 23:
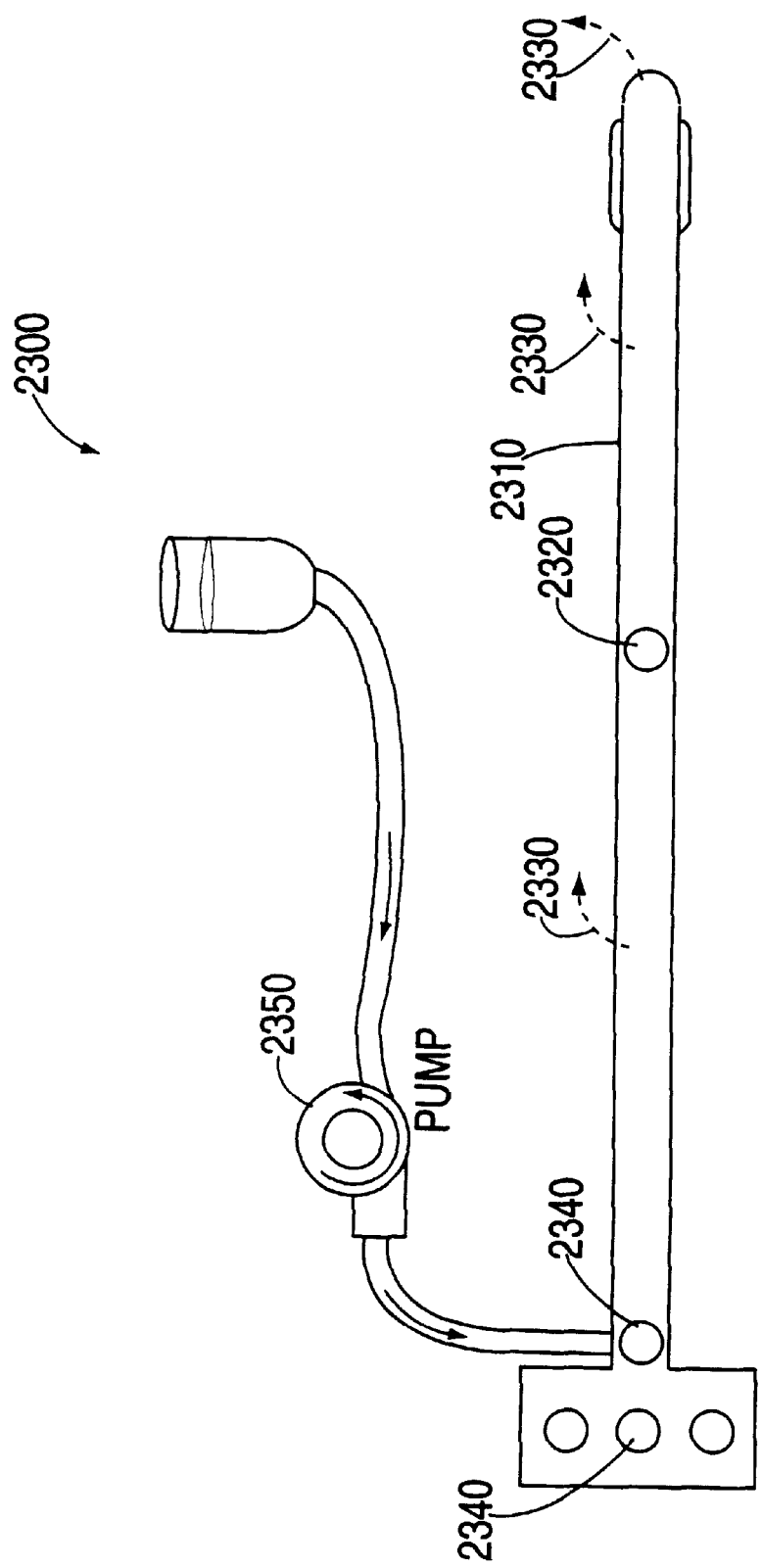
FIG. 23 illustrates a perspective view of a variant of an improved cardiac catheterization and/or angioplasty system 2300 and method of cardiac catheterization and/or angioplasty.

FIG. 23 illustrates a perspective view of a variant of an improved cardiac catheterization and/or angioplasty system 2300 and method of cardiac catheterization and/or angioplasty. Catherization and/or angioplasty catheter 2310 has apertures 2320 that allow for the egress of cholesterol acceptors therefrom. In a variant, catheter 2310 has a permeable membrane that allow for the egress for cholesterol acceptors therefrom. Phantom arrows 2330 indicate egress sites for cholesterol acceptors and/or diagnostic agents. Sites 2340 indicate entry sites for the acceptors or agents. The balloon on the device 2300 can be replaced or supplemented with other devices or can form an inner balloon layer disposed within an outer balloon layer. The acceptors are disposed between the inner and outer flexible balloon layers. Upon expansion of said inner balloon layer a force is exerted against the fluid or gel-like acceptors forcing the acceptors out of the sites 2320, and into direct contact (forcefully) against arterial lesions more locally directing the treatment. It will be appreciated that this variant of the invention provides for maximal penetration of the acceptors into the arterial lesions. The infusions can be accomplished by gravity, manual manipulation of a syringe, or by mechanical infusion pump 2350. The same method and system can be utilized with standard vascular imaging techniques or vessels that include the femorals, carotids, and mesenteric vessels by way of example.

Patient 2210 undergoes cardiac catherization and/or angioplasty. The patient intravenously receives effective doses of cholesterol or lipid acceptors 2230 co-administered with said treatments(s) from container 2220. Intraarterial access of a catheter for coronary angiography and/or angioplasty allows for ready co-administration of lipid or cholesterol acceptors and administration of diagnostic agents such as cholinergic agents, to assess vascular function.

Container 2110 accepts spent fluid from abdomen 2010 by way of channel 2120. The device 2110 provides access to diagnostic samples of spent dialysate to allow for assay of cholesterol, phospholipid, and other parameters as described herein showing the efficacy of the treatments described. Optionally, assay syringe 2130 is inserted by way of access portal 2140 into channel or tube 2120, and optional pumps (not shown) are used to move the various fluids to appropriate locations for assay thereof.

Figure 24:
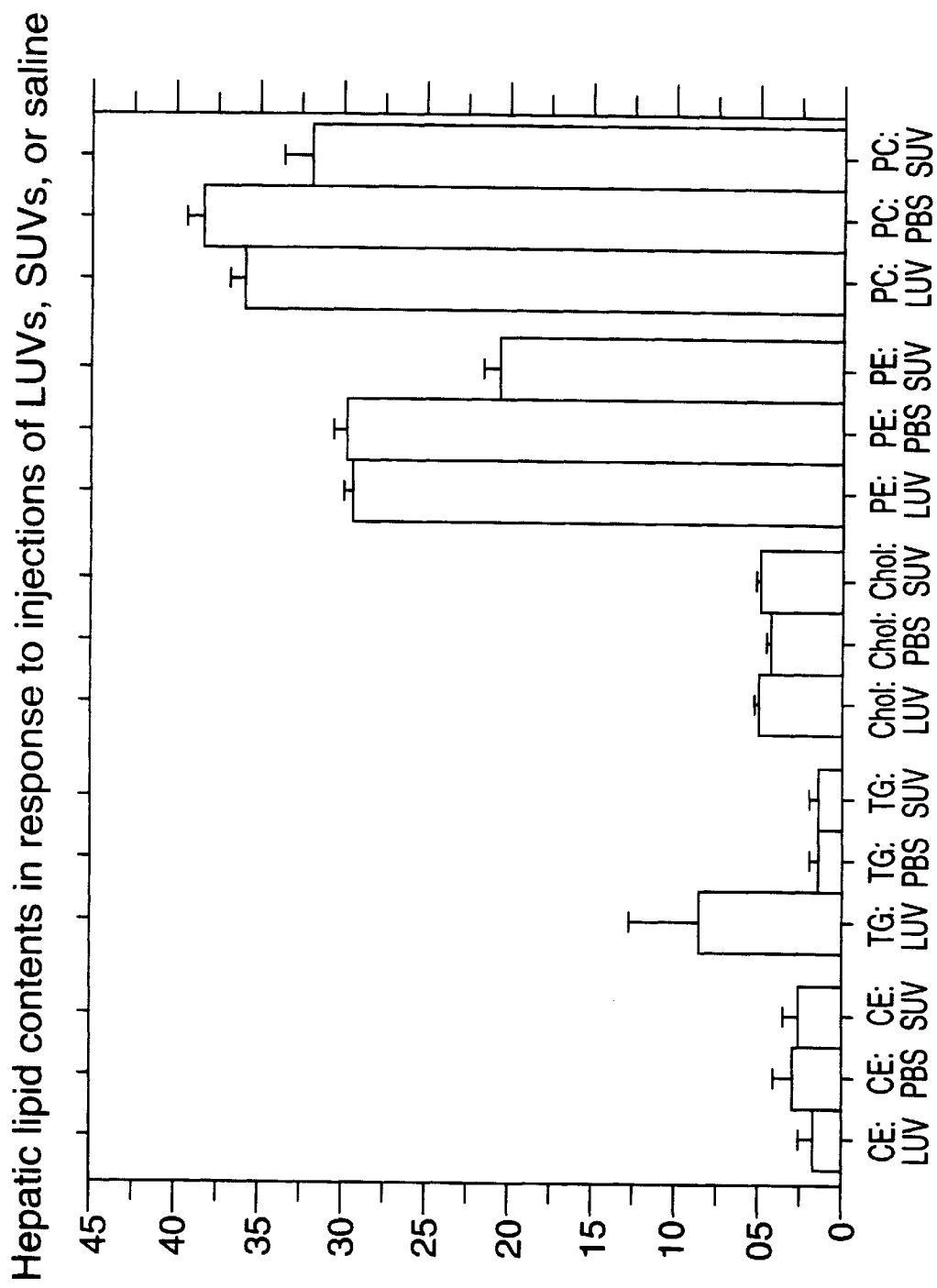
FIG. 24 illustrates a graph of hepatic lipid contents in response to injections of LUVs, SUVs, or saline.

FIG. 24 illustrates a graph of hepatic lipid contents in response to injections of LUVs, SUVs, or saline. The experimental details are as outlined above. Liver samples were assayed for contents of several lipids: cholesterol ester (CE); triglyceride (TG); unesterified cholesterol (Chol); phosphatidylethanolamine (PE); and phosphatidylcholine (PC), which are displayed in units of $\mu$g (micrograms) lipid/mg. Lower values of PE and PC in the SUV-treated animals were produced; thus, the Chol:phospholipid ratios in these animals was higher than in the other groups.

Figure 25:
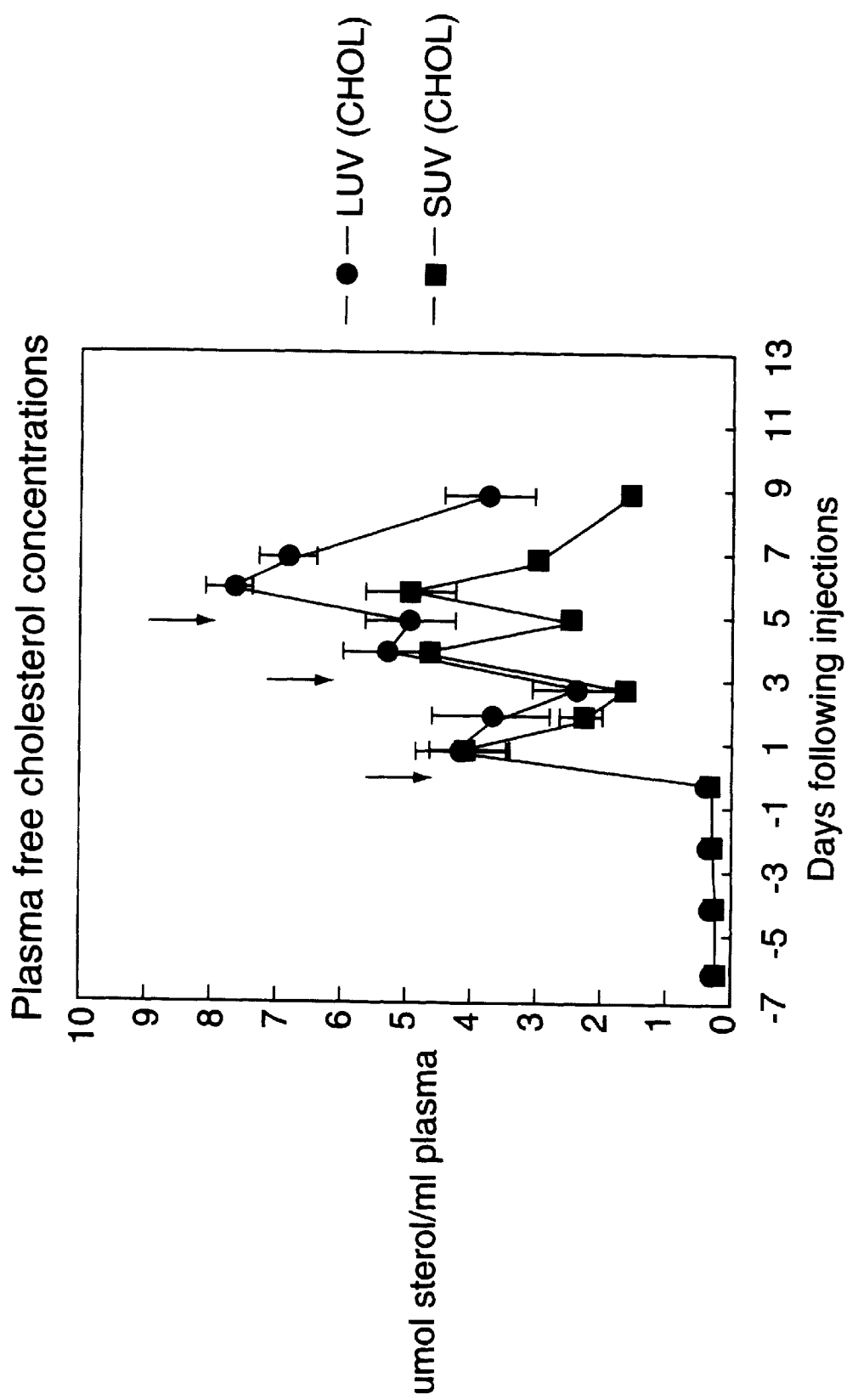
FIG. 25 illustrates plasma free cholesterol concentrations following repeated injections of SUVs or LUV (300 mg/kg) in NZW rabbits.

FIG. 25 illustrates cholesterol ester concentrations following repeated injections of SUVs or LUVs (30 mg/kg) in NZW rabbits (New Zealand White rabbits). The arrows indicate times of phospholipid injection here on days 0, 3 and 5. For a given phospholipid dose, LUVs promote a greater rise in plasma free cholesterol concentrations.

Figure 26:
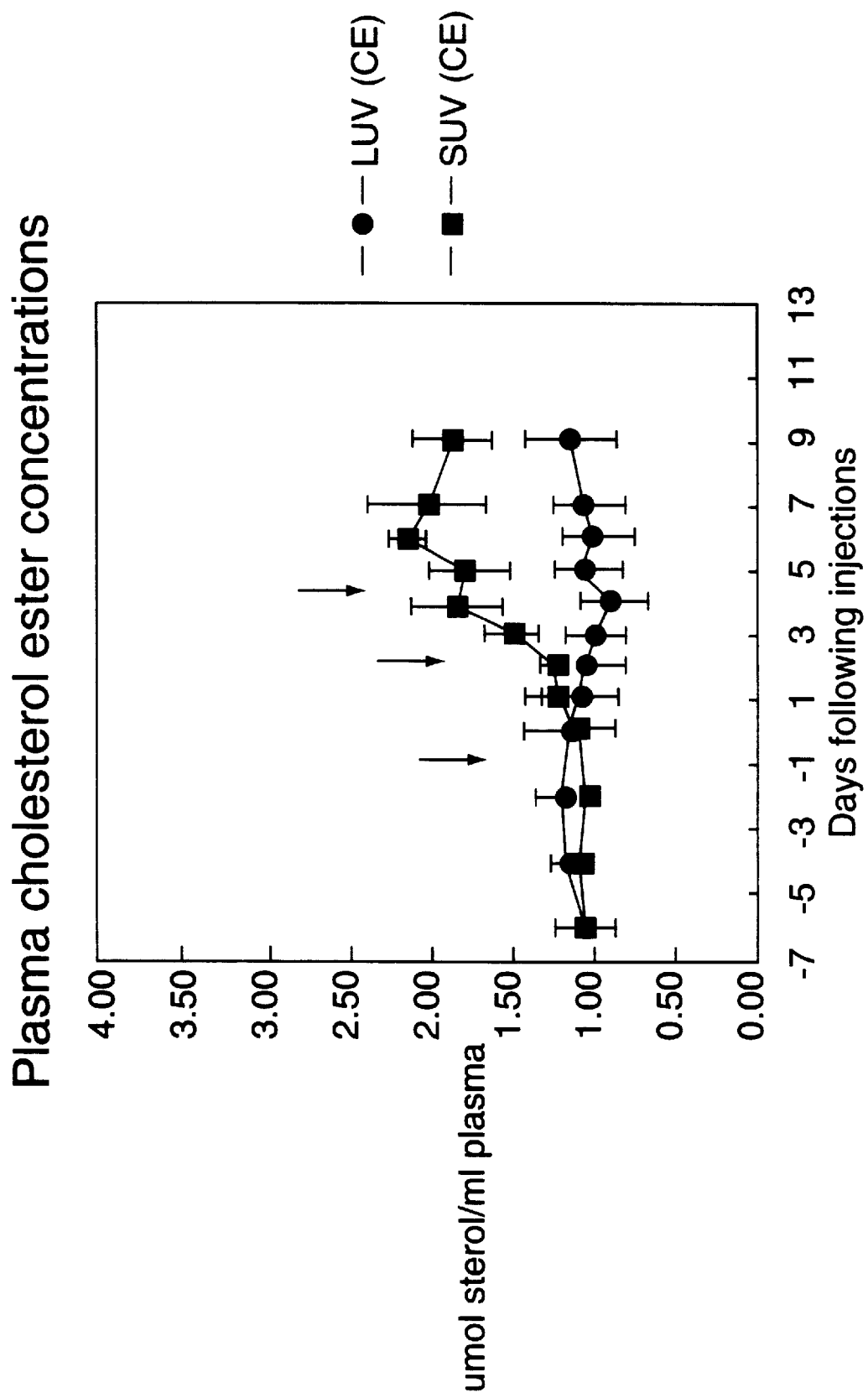
FIG. 26 illustrates plasma cholesterol ester concentrations following repeated injections of SUVs or LUV (300 mg/kg) in NZW rabbits.

FIG. 26 illustrates plasma free cholesterol concentrations following repeated injections of SUV or LUV (300 mg/kg) in NZW rabbits in the same experiment as in FIG. 25, arrows indicate times of phospholipid injection. Repeated injections of LUV, unlike SUV, do not provoke a dramatic rise in CE concentrations in plasma.

The rise in plasma CE concentrations that results from the delivery of excess cholesterol to the liver may be the consequence of two processes. It may involve an overproduction of CE-rich particles or an impaired clearance of CE-rich lipoproteins. Overproduction of CE-rich particles that occurs following SUV infusions may result in the plasma or in the liver. In plasma, LCAT acts on small unilamellar phospholipid vesicles or on phospholipid enriched HDL generating CE which may be subsequently transferred by CETP onto LDL. The results with gel filtration of plasma from animals treated with SUVs indicate that CE is carried mostly or substantially on LDL. Also, in plasma, removal of apoE from VLDL by SUVs will slow the clearance of VLDL, thereby favoring a more efficient conversion into LDL. In the liver, the increased delivery of cholesterol to hepatocytes during cholesterol mobilization stimulates an over secretion of apoB, CE-rich lipoproteins.

In a variant, the rise in plasma CE concentrations observed is the result of an impaired clearance of CE rich atherogenic lipoproteins. Intravenously administered liposomes that acquire apoE compete with LDL for LDL-receptor mediated uptake. The delivery of excess cholesterol to the liver down regulates LDL receptors. The processes responsible for an increase in plasma CE concentrations are different between the two liposome preparations. LUVs, unlike SUVs, do not provoke a rise in plasma CE concentrations. LUVs are superior preparations for mobilizing tissue cholesterol without harmful side effects.

The method and composition of the present invention also provides enrichment of HDL cholesterol esters by SUVs. One contributing process is the stimulation of lecithin cholesterol acyl transferase (LCAT) and other processes related thereto. The ability of SUVs to increase HDL cholesterol ester is the result of stimulation of LCAT and other processes related thereto. LCAT need phospholipid and cholesterol to generate cholesteryl ester and lysophosphatidylcholine; liposomes can supply extra phospholipid. The present invention also provides for alterations in lipoprotein (LDL, HDL, etc.) composition and function by LUVs and/or SUVs and/or other acceptors.

The liposome compositions described herein and methods utilizing same also include the liposomes picking up endogenous apoE and hence blocking cellular uptake of LDL. The liposomes pick up apolipoproteins, such as apoE and apoA-I, and that this alters or enhances their functions. For example, the uptake of endogenous apoA-I enhances the ability of liposomal derived phospholipid to pick up cholesterol, and the uptake of endogenous apoE would allow the liposomes to block certain pathways for arterial uptake of lipoproteins. All of this is in the context of controlling LDL levels and hepatic gene expression and cholesterol homeostasis.

LUVs and SUVs deliver cholesterol to different regulatory pools within the liver. This conclusion is supported by the differences in hepatic gene responses and CETP mRNA is suppressed: the LDL receptor mRNA is unaffected or increased by LUVs but suppressed by SUVs; and CETP is suppressed by LUVs, but unaffected by SUVs. Further, it is understood that the arterial lesions referenced herein include, by way of example, critical stenoses.

The key points about LUVs and atherosclerosis are illustrated in FIG. 9. The practical benefits of using LUVs as a treatment for atherosclerosis are that they are straight forward to manufacture, and non-toxic even at very high doses. Mechanistically, LUVs promote reverse cholesterol transport in vivo without provoking a rise in LDL concentration, and LUVs are an optimal preparation.

The compositions that are used herein can direct clearance away from hepatic parenchymal cells. And the various methods described herein are utilized with slow infusions of the compositions described, so that hepatic cells are not cholesterol overloaded even if clearance by parenchymal cells occurs. Further, HDL is also controlled by CETP gene suppression.

As described herein assays are performed by: assaying fasting plasma triglyceride to estimate VLDL concentrations; assaying plasma cholesterol (free and ester, or total minus free=ester); precipitating LDL (& VLDL) with polyanions-cations; assaying the supernatant which is HDL; and computing LDL's (whole plasma value minus VLDL-HDL) sterol (or sterol ester) in whole plasma. Liposomes will precipitate with polyanions-cations; or optionally assaying the ester which liposomes mostly lack. Other assays include electrophoresis, chromatography, immune assays, electron microscopic assays, functional assays, structural assays, and compositional assays.

In the dialysate of the present invention, any liposomes or emulsions could be used as long as it's a cholesterol acceptor and either it does not raise LDL or it is not returned to the patient's circulation. In either case, one would need to assay plasma LDL and the plasma concentration of the acceptors, and plasma concentrations of other atherogenic lipoproteins.

With respect to the methods that require delivering the cholesterol to the liver at a slow rate, or in low doses administration might permit small acceptors, such as SUVs, to be used without LUVs provided LDL levels as levels of other atherogenic lipoproteins are monitored and regulated. To avoid disrupting hepatic cholesterol homeostasis, the entrapped drug as described herein need not be given at low doses, but rather the encapsulating liposome or emulsion is given in low doses; the drug could be present at high amounts within a small number of liposomes or a small mass of liposomal lipid.

Alterations in HDL size, composition and function can be accomplished by administering high or even truly low doses of large and/or small liposomes that have little or no sterol. Liposomes without sterol, when given in low doses are easily broken apart by HDL and HDL apolipoproteins and then pieces are incorporated into the HDL fraction of plasma enriching it in phospholipid. Such small doses, e.g. 10–100 mg/kg/dose, even of SUVs without LUVs or drugs to lower LDL levels, are unlikely to raise plasma LDL levels, although periodic monitoring would be prudent.

Also, the method as disclosed herein of altering LDL composition without increasing LDL concentration would be to enrich the composition with phospholipids, like POPC (palmitoyloleylphosphatidylcholine), that are resistant to oxidation, enrich the composition with anti-oxidants, deplete unesterified cholesterol, and reduce cellular or arterial uptake of oxidized LDL by phospholipid enrichment.

Liposomes up to about 1000 NM or so would work in the present invention. Larger liposomes would also work but extraction of tissue lipoprotein may be less efficient. It is further possible to concentrate or dry compositions of the present invention. These preparations are then diluted or reconstituted at the time of therapy or administration. In this variant, a two component kit comprising the active material and a dilutent is provided. Inclusion of phosphatidyl glycerol (PG) to make the liposomes negatively charged, or charge other components of the composition, to prevent aggregation during storage is also provided.

Figure 27:
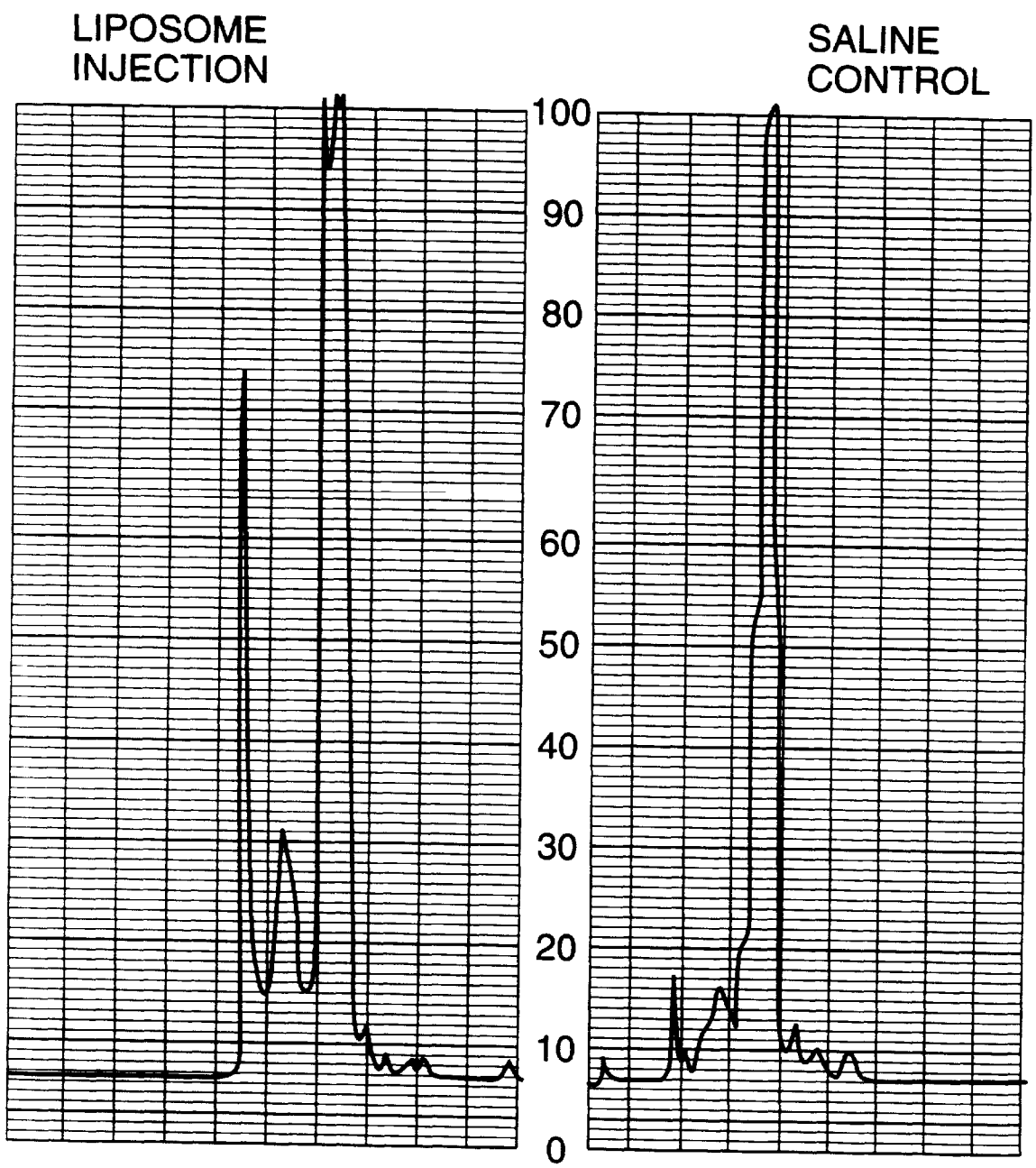
FIG. 27 illustrates alternations in plasma components after repeated injections of SUVs; and, FIG. 28 illustrates an agarose gel electrophoresis of whole plasma following repeated injections of LUVs, SUVs, or saline.

FIG. 27 illustrates alterations in plasma components after repeated injections of SUVs. Watanabe Heritable Hyperlipidemic (WHHL) rabbits were given intravenously 1000 mg of SUV phospholipid per kg of body weight, or the equivalent volume of saline, on Monday, Wednesday, & Friday of each week for three weeks (nine doses total). Three days after the final dose, blood samples were taken, and plasma components were fractionated by size by passage over a Superose-6 gel-filtration column. Eluents were read by an in-line spectrophotometer. The tracing on the right is from a saline-injected rabbit, and shows VLDL around fractions #17–18, and LDL around fraction #27. The tracing on the left is from an SUV-injected rabbit, and shows VLDL with persistent liposomes around fraction #16, and LDL-sized particles around fraction #25. The tracings indicate an increase in the amount of LDL-sized particles after repeated injections of SUVs, consistent with an increase in LDL, which is a harmful effect. Because WHHL rabbits have a genetic lack of LDL receptors, this result indicates that SUVs disrupt hepatic cholesterol homeostasis not just by suppressing LDL receptor (FIG. 5), but also by mechanisms independent of LDL receptors (FIG. 27). LUVs avoid both LDL receptor-dependent and independent disruptions.

Figure 28:
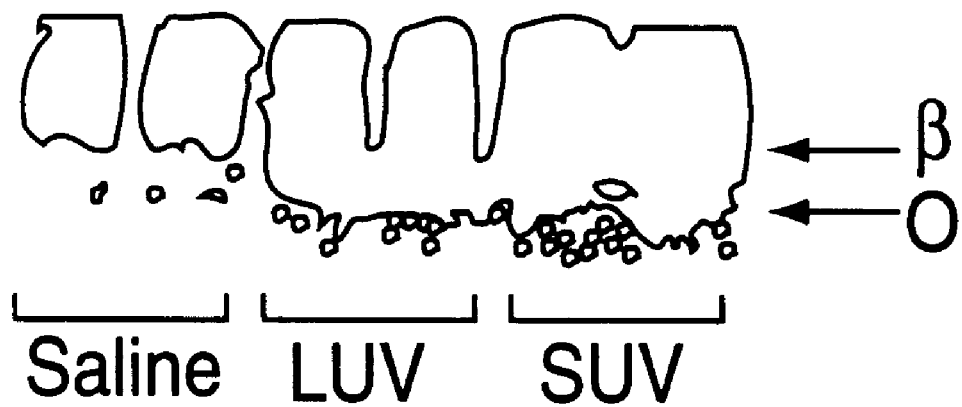

FIG. 28 illustrates an agarose gel electrophoresis of whole plasma following repeated injections of LUVs, SUVs, or saline. Experimental details are referenced in FIGS. 2–8 & elsewhere herein. Four-$\mu$L plasma samples from two rabbits in each group at day 6 were electrophoresed through 1% agarose then stained for lipids with Sudan black. O: origin. $\beta$: migration of an LDL standard. The SUV-mediated increase in LDL concentration is illustrated by the darker but otherwise unremarkable i-band in those lanes. SUVs in plasma exhibited a mobility ahead of LDL, owing to their acquisition of plasma proteins, chiefly from HDL. In contrast, plasma LUVs exhibited essentially the same mobility as freshly prepared, protein-free vesicles, i.e., just above the origin (O), indicating a substantial absence or reduction of acquired proteins on the LUVs.

Based on the electrophoretic mobilities in FIG. 28, quantification of the acquisition of protein by LUVs versus SUVs was obtained. LUVs and SUVs were incubated with human HDL in vitro for 4 hours at 37° C. then separated from the HDL by gel filtration chromatography and assayed for protein and phospholipid. LUVs acquired 1.09 $\mu$g of protein per mg of liposomal phospholipid, whereas SUVs acquired 40.4 $\mu$g/mg, i.e., almost 40 times as much. Thus, the two types of liposomes exhibit a striking quantitative difference in protein adsorption. SUVs, but not LUVs, avidly strip apoE from VLDL, thereby slowing its clearance from plasma and favoring its conversion to LDL. In addition, adsorbed proteins play a role in directing the SUVs into a hepatic metabolic pool that disrupts hepatic cholesterol homeostasis, whereas LUVs are not directed into such a pool. Liposomes, emulsions, or any other particles or compounds that extract tissue lipids but do not acquire large amounts of plasma proteins behave similarly to LUVs in these regards.

Specific vascular genes affected by cholesterol loading of cells include genes for prolyl-4-hydroxylase; hnRNP-K; osteopontin (there may be a role for oxidized lipids in provoking arterial calcifications); and Mac-2. The methods of regulating these genes described herein effect restoration of normal vascular or arterial function. Elevated expression of prolyl-4-hydroxylase (an enzyme in the synthesis of collagen, a component of fibrotic plaques) and hnRNP-K (identified in pre-mRNA metabolism and cell cycle progression) messages were found in aortic smooth muscle cells after cholesterol feeding. These would normalize after the liposome treatments described herein. Other genes or enzymes that are abnormal with cholesterol-loading and should normalize with liposome treatment as described herein include osteopontin, nitric oxide synthase (NOS), adhesion molecules, chemoatractants, tissue factor, PAI-1 (plasmidigen activator inhibitor), tPA (tissue plasmidigen activator) and Mac-2 (Ramaley et al. 1995). Other genes affected by cholesterol, cholesterol loading, oxidized lipids would also be corrected.

Many examples of small acceptors such as SUVs, apolipoprotein-phospholipid disks, and HDL are commercially available and can be used in the invention. Kilsdonk EP et al. Cellular cholesterol efflux mediated by cyclodextrins, J. Biol. Chem. 270:17250–17256, 1995. By way of further example, another small acceptor includes the cyclodextrins. Small acceptors (specifically HDL) shuttle cholesterol from cells to liposomes. Cyclodextrins and also other small acceptors can shuttle cholesterol and other exchangeable material from cultured cells to LUVs, which substantially increases the removal and donation of material between cells and LUVs.

Examples of anti-hyperlipidemic drugs include fibric acid derivatives, HmG CoA reductase inhibitors, Niacin, probucol, bile acid binders, other drugs and combinations thereof. Anti-hyperlipidemic treatments also include LDL, apheresis, ileal bypass, liver transplantation and gene therapy.

The data presented in this application support three possible explanations for the difference in metabolic response to LUVs versus SUVs. The three mechanisms act separately or in combination. First, LUVs are taken up largely by Kupffer cells, whereas SUVs are primarily directed towards hepatic parenchymal cells. This is partly a mechanical consequence of hepatic architecture: hepatic endothelial fenestrae are oval openings of about 100×115 nm, through which SUVs of 30-nm diameter or so can readily pass and gain access to parenchymal cells. Large particles, such as large liposomes, of sufficient diameter will not pass easily, and are cleared instead by the macrophage Kupffer cells that line the liver sinusoids. While SUVs also have access to Kupffer cells, their sheer number (~10 times as many SUVs as LUVs per mg of phospholipid) appears to saturate the reticuloendothelial system, and so parenchymal cells predominate in their clearance. Other methods to direct artificial particles away from parenchymal cells are also available, such as by changing the particle structure or composition, including charge and specific ligands for cell-specific binding.

Cholesterol clearance pathways mediated by parenchymal versus Kupffer cells have distinct metabolic consequences. Direct delivery of cholesterol to parenchymal cells by SUVs suppresses sterol-responsive messages (FIGS. 5, 6, & 8). Delivery of cholesterol to Kupffer cells can be followed by gradual transfer of lipid to parenchymal cells, for example, via the extensions of Kupffer cells that reach down through the space of Disse to make physical contact with parenchymal cells. The rate of sterol delivery to the parenchymal cells by transfer from Kupffer cells can be slower than by direct uptake; the chemical form of the sterol may be altered by the Kupffer cells before transfer; there is other cell-cell communication; and, based on other pathways for lipid transfer amongst liver cells, the process of transfer from Kupffer to parenchymal cells may be regulated, whereas SUV clearance does not appear to be.

The second contributing explanation for the difference in metabolic response to LUVs versus SUVs is based solely on differences in the kinetics of their delivery of cholesterol to the liver. LUVs are cleared from plasma somewhat more slowly than are SUVs, and thereby produce a relatively constant delivery of cholesterol mass to the liver from the time of injection until the bulk of injected material is cleared. SUVs are cleared more rapidly, thereby delivering a large bolus of cholesterol mass to the liver several hours after each injection, which is followed by the sustained rise in plasma concentrations of cholesteryl ester and atherogenic lipoproteins. The slow, steady delivery by LUVs avoids disrupting hepatic cholesterol homeostasis, while the more rapid uptake of SUV cholesterol overwhelms the ability of the liver to maintain homeostasis, thereby provoking suppression of hepatic LDL receptors. Other methods to deliver artificial particles or their components to the liver at a proper rate are also available, such as by changing the particle structure or composition, including charge and specific ligand for cell-specific binding.

The third contributing explanation is based on the striking quantitative difference in protein adsorption between the two types of vesicles (FIG. 28), which, in that particular experiment, was a result of their distinct surface curvatures. Thus, SUVs, but not LUVs, would avidly strip apoE from VLDL, thereby showing its clearance from plasma and favoring its conversion to LDL. SUVs that acquire apoE will compete with VLDL, LDL, and other particles for receptor mediated uptake by the liver. Also, adsorbed apoproteins can play a role in directing phospholipid vesicles to different hepatic metabolic pools. Other methods to reduce protein uptake by artificial particles are also available, such as by changing the particle structure or composition, including charge and specific ligands for cell-specific binding.

Overall, given the observation that cholesteryl ester and LDL concentrations do not increase after delivery of large amounts of cholesterol and other exchangeable material to the liver by LUVs, it was apparent that delivery was to a specific metabolic pool or pools with unique properties that do not increase plasma concentrations of atherogenic lipoproteins or harmfully disturb hepatic cholesterol homeostasis, including the regulation of genes and other functions. Thus, these inventions can be regarded in part as a unique delivery system that brings original particle components, such as phospholipid, plus material acquired by the particles, such as cholesterol, to a specific delivery site for harmless disposal and other additional benefits. The delivery system with these characteristics will be useful in any situation whatsoever in which control of hepatic cholesterol homeostasis, hepatic phospholipid homeostasis, and hepatic metabolism in general is advantageous.

For example, in a situation in which it is desirable to modify erthyrocyte lipids, a straightforward approach would be to administer artificial particles that can donate and remove the appropriate lipids. If SUVs are used for this purpose, however, they will transport cholesterol and other material to the liver in a harmful manner, to the wrong pool and/or at the wrong rate, and this will cause increases in plasma concentrations of atherogenic lipoproteins, which is an undesirable side-effect that would preclude this approach. In contrast, the use of large liposomes or other particles with similar properties will result in the proper delivery of original and acquired material, to the proper pool(s) at a proper rate, so that the desired effect (modification of erythrocyte lipids) can be achieved without harmful increases in plasma concentrations of atherogenic lipoproteins.

As another example, it can be desirable to modify infectious agents, such as bacteria, fungi, and viruses, using the compositions and method described herein. Administration of large liposomes or other particles with similar properties will remove and donate exchangeable materials to and from these infectious agents, and then the administered particles will be delivered to the proper pool(s), so that the desired effect can be achieved without harmful increases in plasma concentrations of atherogenic lipoproteins.

As another example, a valuable therapy may provoke an increase in plasma concentrations of atherogenic lipoproteins as an unwanted side-effect. Administration of large liposomes or other particles with similar properties will alter this response through the delivery of lipids and other material to the proper hepatic metabolic pool. The data with the "Mix" animal provides a specific example of this effect (FIG. 4).

There are several mechanisms for affecting arterial uptake, accumulation, and retention of lipoproteins. Liposomes can pick up apoE from atherogenic lipoproteins, thereby reducing lipoprotein binding to arterial cells and also competing for binding to arterial cells. Finally, alterations in LDL size and/or composition affect its binding to extracellular matrix and affect subsequent, harmful alterations within the arterial wall, for example, susceptibility to oxidation or enzymatic modifications.

The action or mode of operation of large acceptors, such as large liposomes, can be aided by small acceptors, and vice-versa, and this applies to both endogenous (e.g., HDL) and exogenous (e.g., apoprotein-phospholipid complexes) small acceptors. Large acceptors penetrate poorly into the interstitial space and appear to inefficiently approach the cell surface under certain circumstances. These effects impede their uptake and donation of exchangeable material from membranes, cells, tissues, organs, and extracellular regions and structures. Small acceptors do penetrate well into the interstitial space and are able to approach the cell surface, thereby allowing efficient uptake of exchangeable material. Small acceptors have major disadvantages, however. They have a very limited capacity to acquire or donate material (even though the initial rate of acquisition or donation is rapid, until their capacity becomes saturated) and, once they have acquired material, they deliver it to the liver in a way that disrupts hepatic cholesterol homeostasis.

Large acceptors and small acceptors together, however, synergistically overcome each other's drawbacks through at least three mechanisms. First, the large acceptors act as a sink (or supply) for exchangeable material, while the small acceptors act as a shuttle that siphons material from peripheral stores to the large acceptors and in the other direction. Thus, for example, the small acceptors penetrate tissue, acquire (and/or donate) material from the tissue, and their capacity becomes at least partly saturated. They leave the tissue and encounter the large acceptors in the plasma, at which point the small acceptors are stripped of tissue lipids. The capacity of the small acceptors is thereby restored, so that when they return to the tissue, they can acquire (and/or donate) more material. This cycle can continue many times. Second, the large acceptors can re-model some small acceptors. For example, large acceptors can donate phospholipid to HDL, which increases the capacity of HDL acquire tissue cholesterol and other material. Third, as noted elsewhere, the presence of large acceptors can block or reduce the harmful disruptions in hepatic cholesterol homeostasis caused by the small acceptors.

Large liposomes avoid raising plasma concentrations of atherogenic lipoproteins in general, not just LDL. This list includes all lipoproteins that contain apolipoprotein B (apoB), such as LDL, IDL, VLDL, Lp(a), $\beta$-VLDL, and remnant lipoproteins.

Immune cells are also the targets for depletion using the methods and modes of operation disclosed herein. It is understood that administration of an HMG-CoA reductase inhibitor, pravastatin, to cardiac transplant recipients reduced their natural-killer-cell cytotoxicity in vitro, reduced episodes of rejection accompanied by hemodynamic compromise, reduced coronary vasculopathy, reduced plasma LDL levels (and increased HDL levels), and significantly enhanced one-year survival. The effect on survival was dramatic: in the control group, 22% died in the first year, whereas only 6% died in the pravastatin-treated group.

Immunologic effects of HMG-CoA reductase inhibitors have been reported in vitro. These reported immunologic effects include the regulation of DNA in cycling cells, the inhibition of chemotaxis by monocytes, the regulation of natural-killer-cell cytotoxicity, and the inhibition of antibody-dependent cellular cytotoxicity. Regulation of such inhibitors results from changes in circulating lipids or other effects and by utilization of the methods and modes of operation disclosed herein.

HMG-CoA reductase catalyzes an early step in cholesterol biosynthesis and is crucial in the synthesis of molecules besides cholesterol. Adding cholesterol to immune cells treated with HMG-CoA reductase inhibitors does not restore function, although the addition of mevalonate does. Although this suggests that cholesterol depletion is not directly responsible for the immune effects, the use of liposomes or other acceptors to remove cholesterol from cells increases endogenous consumption of mevalonate, as the cells try to make more cholesterol. To impede the ability of the immune or other cells to make up their cholesterol loss by picking up more LDL or other lipoproteins, the methods and treatment described herein are also be done in conjunction with therapies to lower plasma cholesterol concentrations (including HMG-CoA reductase inhibitors, fibric acids, niacin bile acid binders, LDL-pheresis, etc.).

These processes include enhancement of cholesterol removal and reduction of cholesterol influx. Levels of HDL, the apparent natural mediator of cholesterol removal from peripheral cells, increased in a treated group of patients, and LDL levels were deceased. The administration of HMG-CoA reductase inhibitors in vivo usually causes very tiny changes in reductase enzyme activity: cells simply make more enzyme to overcome the presence of the inhibitor. They also make more LDL receptors (especially in the liver) and so LDL levels fall.

The invention further provides for additives to PD (peritoneal dialysis solutions) that reduce the accelerated atherosclerosis that occurs in renal failure.

Chemotaxis of monocytes is an important early event in atherosclerotic lesion development: monocytes become attracted to abnormal arterial lipid deposits, and to cellular products made in response to the presence of these deposits, enter the vessel wall, transform into macrophages, internalize the lipid by phagocytosis and/ole endocytosis, and become a major component of the so-called lipid-rich foam cells of human atherosclerotic lesions. Thus, inhibition of monocyte chemotaxis is important for atherosclerosis as well and can be accomplished using the methods disclosed herein. Both cellular and humoral immunity seem to be affected by reductase inhibition: cardiac rejection accompanied by hemodynamic compromise has often been associated with humoral rejection (i.e., that occurring without producing marked lymphocytic infiltration in endomyocardial-biopsy specimens).

Pravastatin may interact with cyclosporine [an important immunosuppressive drug], which blocks the synthesis of interleukin-2 in stimulated T-lymphocytes. The addition of interleukin-2 restored the natural-killer-cell cytotoxicity and partly restored the antibody-dependent cytotoxicity that were inhibited in lovastatin-treated in vitro cell cultures. A synergy between cyclosporine and pravastatin explains increased immunosuppression in recipients of cardiac transplants, whereas patients without transplants who receive HMG-CoA reductase inhibitors for hypercholesterolemia do not have clinical immunosuppression.

Thus, the use of safe cholesterol acceptors with other immunosuppressives, such as cyclosporine &/or glucocorticoids (which can also suppress IL-2) is also contemplated by this invention.

It is also appreciated that the invention utilizes derivatives of various compounds described herein.

Pathological specimens from patients with cardiac transplants who have severe coronary vasculopathy have been reported to have a high cholesterol content. Therefore, early cholesterol lowering with pravastatin may play a part in decreasing the incorporation of cholesterol into the coronary arteries of the donor heart. Large liposomes or other cholesterol acceptors are used to accomplish the same effect, quickly and directly, alone or in combination, therewith.

Immune modulations is important in many conditions, not just cardiac transplantation. Areas in which the above approaches could be used also include transplantations of other organs, autoimmune diseases (in which the body's immune system mistakenly attacks the body's own tissues), some infections (in which the immune reaction becomes harmful), and any other situation in which immune modulation would be helpful.

With respect to infections, modification of the lipid content and composition of foreign objects in the body (such as infectious agents) while maintaining normal hepatic cholesterol homeostasis should also be mentioned.

Oxidized lipids alter tissue function and cause damage, including decreased EDRF, and increased adhesion molecules, cell damage, and macrophage chemotaxis.

There are interactions between LUVs and small acceptors, such as HDL, apoprotein phospholipid complexes, and cyclodextrins. Liposomes remodel HDL into a better acceptor by donating extra phospholipid, and the small acceptors act as a shuttle, carrying cholesterol efficiently from cells to liposomes. LUVs do not elevate LDL concentrations and do not suppress hepatic LDL receptor gene expression. The medical utility for LUVs includes restoring EDRF secretion by endothelial cells. High cholesterol levels inhibit endothelial release of EDRF not through cholesterol, but through an oxidized derivative of cholesterol. Because HDL itself restores EDRF release, perhaps through the removal of cholesterol or of oxidized lipids, then liposomes would be able to do the same (the HDL ferries cellular oxidized lipids to liposomes, for example).

The invention provides a method and mode of operation for modifying cellular lipids, including oxidized lipids, without provoking a rise in LDL concentrations or harmfully disturbing hepatic homeostasis. Thus, the LUVs, presumably acting in concert with endogenous (or exogenous) small acceptors of cholesterol (such as HDL), pull oxidized lipids out of peripheral tissues and deliver them to the liver for disposal. Oxidized lipids have a wide range of harmful biological effects, including suppression of EDRF release, induction of cell adhesion molecules, cellular damage, chemotaxis of macrophages, and so forth.

Oxidized lipids and their harmful effects include decrease endothelial C-type ANF; increased endothelial PAI-1 and decreased tPA and decreased endothelial thrombomodulin. Liposomes enhance or participate in this effect. These changes impair the body's ability to dissolve clots. The methods disclosed herein assist in ameliorating these harmful effects of oxidized lipids. HDL acts in part by transporting enzymes that inactivate biologically active oxidized lipids.

It is understood that oxidized LDL inhibits endothelial secretion of C-type natrizuretic peptide (CNP). It is the lipid component of oxidized LDL that mediates this effect. Most importantly, HDL blocks the action of oxidized LDL, presumably by picking up oxidized lipids (e.g., oxidized cholesterol). Coincubation with high-density lipoprotein (HDL), which alone had no effect on CNP release, significantly prevented Ox-LDL-induced inhibition of CNP secretion by endothelial cells (ECs). Analysis by thin-layer chromatography demonstrated that oxysterols, including 7-ketocholesterol, in Ox-LDL were transferred from Ox-LDL to HDL during coincubation of these two lipoproteins. These results indicate that Ox-LDL, suppresses CNP secretion from ECs by 7-ketocholesterol or other transferable hydrophilic lipids in Ox-LDL, and the suppressive effect of Ox-LDL is reversed by HDL.

Whatever molecule HDL picks up, the presence of liposomes or other acceptors around as described herein will allow it to do a better job, because of remodeling of HDL by liposomes & shuttling of oxidized lipids by HDL from tissues to liposomes (i.e., the liposomes continuously strip the HDL). Liposomes with an exogenous small acceptor will also work.

It is further understood that transferable lipids in oxidized low-density lipoprotein stimulate plasminogen activator inhibitor-1 and inhibit tissue-type plasminogen activator release from endothelial cells. As above, it is the lipids in oxidized LDL, such as oxidized forms of cholesterol, that produce the effect. It is understood that oxidized low density lipoprotein reduced thrombomodulin transcription in cultured human endothelial cells. It is appreciated that oxidized lipids play a role in atherosclerosis, and enzymes on HDL that inactivate oxidized lipids may contribute to a protective effect. It is contemplated that the methods and compositions disclosed herein will help this proposed mechanism as well, for example, by removing end-products of these enzymes, by otherwise altering HDL, and by providing an additional platform for enzyme transport and action.

As such the use of large liposomes to remove harmful lipids in general (here, oxidized lipids) from peripheral tissues, either directly or via HDL, which would extract the lipids first, possibly inactivate them, then deliver them or their break-down products to liposomes in the circulation is described. Direct methods to assess oxidation and oxidative damage in vivo include for lipids, assays for 8-epiPGF$_2$alpha; for DNA, assess 8-oxo-2' deoxyguanosine; generally assess anti-oxidant enzymes in tissues; and assess anti-oxidants levels, such as vitamin E, vitamin C, urate, and reduced/oxidized glutathione.

Methods relating to and modes for effecting the reverse lipid transport, from cells, organs, & tissues, including transport of extracellular material, and any exchangable material in general are described herein. This covers not just cholesterol, but also sphingomyelin, oxidized lipids, lysophophatidylcholine, proteins, and also phospholipid donation. Some effects of oxidized material include increased calcification in arterial cells as described above and below.

Three potential differences between large versus small liposome to explain their different effects on LDL and apoB levels include: fenestral penetration (LUV<<SUV); rate of clearance (LUV<SUV, so that LUVs produce a slow, sustained cholesterol delivery to the liver that may be less disruptive); and protein adsorption (LUV<<SUV).

Unesterfied cholesterol increases tissue factor expression by macrophages. This is extremely important, because it is macrophage-derived tissue factor that makes the material released by unstable, rupturing plaques such a powerful stimulus for a clot to form that then blocks the vessel leading to a heart attack. The methods and modes of operation and compositions of the invention act upon the expression of tissue factor.

Poor absorption of proteins by large liposomes affects LDL levels and/or atherosclerosis by the following mechanisms: 1) acquisition of apoE from VLDL by small liposomes impairs the removal of VLDL from the circulation, thereby allowing it to be more efficiently converted into atherogenic LDL; ii) absorbed proteins on small liposomes direct these particles into the wrong metabolic pool within the liver. Polyacrylamide gel electrophoresis shows that liposomes (actually small liposomes) increase the size of LDL. Liposomes are used to alter LDL size, composition and structure to decrease its atherogenicity.

Other properties of LDL could be changed by administration of liposomes. For example, liposomes reduce surface unesterified cholesterol; reduce surface sphingomyelin; replace surface phospholipids with POPC which is poorly oxidized; supplement the LDL with antioxidants that were added to the liposomes before administration. These changes would substantially alter arterial entry, retention, modification and atherogenicity of LDL.

The side-effects controlled are focused on hepatic cholesterol metabolism, hepatic expression of genes involved in cholesterol metabolism, and plasma concentrations of cholesterol-rich atherogenic lipoproteins that contain apolipoprotein B (chiefly, LDL). Reverse transport of sphingomyelin, for example, changes hepatic cholesterol metabolism (cellular sphingomyelin affects the intracellular distribution of cholesterol, and hence its regulatory effects; also sphingomyelin is a precursor to ceramide, which mediates intracellular signaling), though large liposomes appear to avoid any problems in the area. The same holds true for reverse transport of oxidized forms of cholesterol (they are even more potent that unoxidized cholesterol in suppressing LDL receptor gene expression). Cyclodextrins do not pick up phospholipids.

Liposomes pick up any exchangeable lipid (actually, any exchangeable amphipathic or hydrophobic material, which includes lipid or protein or anything else with these characteristics). This includes sphingomyelin, oxidized or modified lipids, such as oxidized sterols and phospholipids. Typically, such liposomes can pick up unesterified cholesterol and other exchangeable material from other lipid bilayers, such as cell membranes, and from lipoproteins. Liposomes also pick up proteins and donate phospholipids. During and after these modifications, the liposomes are removed from the plasma, chiefly by the liver. Throughout this application, we will refer to this general process as "reverse lipid transport", although it is understood that any exchangeable material in tissues, blood, or liposomes could participate. Specific examples of exchangeable material include unesterified cholesterol, oxidized forms of cholesterol, sphingomyelin, and other hydrophobic or amphipathic material.

These molecules accumulate in atherosclerosis and mediate harmful effects (e.g., cholesterol, oxidized cholesterol, and other material, such as lysophospholipids) or in aging (e.g., sphingomyelin). For example, oxidized lipids, particularly sterols, alter many peripheral tissue functions, including stimulating calcification by arterial cells in atherosclerosis & stimulating endothelial plasminogen activator inhibitor-1 release by endothelial cells; other oxidized lipid products include lysophospholipids that stimulate endothelial expression of adhesion molecules that attract macrophages into lesions, and sphingomyelin accumulates in some cell-culture models of aging and, with cholesterol, may account for some of the cellular changes. Other changed, such as oxidation, may also mediate or accelerate aging. Many of these molecules have been shown to be picked up by liposomes in vitro (e.g., cholesterol, sphingomyelin, & probably oxidized cholesterol) and many by HDL (cholesterol, oxidized cholesterol by liposomes) but it is likely that they pick up these other molecules as well. In terms of total mass, however, the bulk of the acquired material is unesterified cholesterol, with proteins in second place. Alternatively, by acquiring unesterified cholesterol, the liposomes may reduce the amount of oxidized cholesterol that develops, because there will be less starting material.

The effective periods of time described herein should not be interpreted to exclude very long courses of treatment, lasting years, for example. Nor should it exclude repeated courses of treatment separated by weeks, months, or years.

Side effects include overload of the liver with cholesterol or other materials acquired by the liposomes; with subsequent alterations in hepatic function, such as suppression of LDL receptors, stimulation of intrahepatic cholesterol esterification, stimulation of intrahepatic cholesterol esterification, stimulation of hepatic secretion of atherogenic lipoproteins that contain apolipoprotein-B, and impaired uptake of atherogenic lipoproteins by the liver from plasma.

As used herein the word, "endogenous" indicates that the HDL arises from within the body, and is not itself administered. HDL and related acceptors can, however, be administered.

The data indicates another difference between large and small liposomes in vivo. Before injection, the liposomes that are used in our experiments were essentially electrically neutral. indicated by a failure to migrate rapidly through a gel of agarose when an electric field is applied. (This does not imply that charged liposomes or other particles could not be used. The small liposomes pick up proteins and other material, and become electrically charged: they now rapidly migrate through agarose gels when an electric field is applied. Agarose gels of plasma samples we had stored from the three groups of rabbits were run. The small liposomes became more mobile LDL in these gels. The large liposomes were substantially less mobile, indicating a lower charge density, reflecting a lower protein content.

Two explanations for the difference between large and small liposomes exist: 1) small ones penetrate through hepatic endothelial fenestrae while large ones do not (thus, large ones go to Kupffer cells and small ones go to hepatic parenchymal cells and cause problems); 2) large liposomes are known to be cleared by the liver somewhat more slowly than are small liposomes (the reason is not known), and so may not overwhelm the liver as easily. The data on charge density provides an explanation in part: less protein, therefore slower or altered hepatic uptake.

The delivery of cholesterol to the liver by LUVs is actually more efficient than by SUVs, per mg of phospholipid. One difference is that the delivery by LUVs is steady over a long period after the injection, whereas the delivery by SUVs peaks then falls.

Some of the composition described herein include egg phosphatidylcholine; synthetic phosphatidylcholines that are not crystalline at body temperature (e.g., they contain at least one double bond) yet are resistant to oxidation (e.g., they do not have many double bonds, such as 1-palmitoyl, 2-oleyl phosphatidylcholine, abbreviated POPC); other natural or synthetic phospholipids alone or in mixtures; any of the preceding supplemented or replaced with hydrophobic or amphipathic material that still allows a liposomal or micellar structure. An extruder is certainly not the only conceivable method for making large liposomes or even particularly LUVs. Other methods known to practioners in the field are available or can be adapted to make large liposomes in general and LUVs in particular.

As used herein, a dose includes from 10 to 1600 mg of phospholipid, in the form of large liposomes, per kg of body weight. Other acceptable rates described herein can be determined empirically by the response of plasma LDL concentrations.

Where there is a change in membrane composition, as well as function, one can use an assay of membrane composition or an assay of tissue composition. Compositional assays should include lipids, proteins, and other components.

HDL can pick up oxidized material, and HDL-associated enzymes may inactivate oxidized material.

The separations in time will depend on the actual dose of material, its effects on hepatic cholesterol homeostasis, and whether cholesterol-lowering agents are being concurrently administered. Thus, for doses of about 300 mg of small liposomes per kg of body weight, slight disruptions will occur after even a single dose, and single administrations of higher doses may cause even more disruptions. Exemplary separations in time include one day to one month, but the precise schedules would have to be determined by monitoring hepatic cholesterol metabolism and plasma levels od LDL and other atherogenic lipoproteins.

The major macrophages that would be involved in liposomal clearance would be Kupffer cells in the liver and macrophages in the bone marrow or spleen. The catabolism here would be the so-called alternative pathway for initiating the conversion of cholesterol into bile acids (macrophages are known to have at least one cholesterol-catabolizing enzyme), or would be transfer of sterol (enzymatically altered or not) to other cells, such as hepatic parenchymal cells that would then dispose of the molecules.

The methods described herein also control effects of cellular aging.

The invention includes means for assessing the efficacy of liposomal therapy by performing assays of oxidation in vitro and in vivo, assays of oxidative susceptibility of plasma components, and assays of the ability of altered HDL to inhibit oxidation (by binding oxidative products and/or through its paroxinase or other anti-oxidant components), and the ability of HDL or plasma or serum or blood to mobilize cholesterol and other exchangeable material.

Large liposomes may cause the mobilization of some material that is trapped between cells as well (this is the extracellular space). This extracellular material causes problems a) when it contacts cells or platelets, altering their function and b) by simply taking up space.

Estimate rates of cholesterol mobilization can be empirically determined. It is appreciated that the kinetics of liposomal clearance is different in different species (the $t_{1/2}$ of LUVs in mice is about 8 h, but in rabbits it is about 24 th, and in humans it is longer). Thus, rates calculated may vary from species to species. Based on my data on injection of 300 mg of SUVs into rabbits, the peak rate of liposomal cholesterol removal from plasma was between 3 h and 6 h after the injection. At that point, the liposomes had raised plasma unesterified cholesterol by just over 2 mmol/L; assuming a total plasma volume of 90 mL in a 3-kg rabbit, the total liposomal cholesterol at that point was 180 umoles; the $t_{1/2}$ for SUVs in these rabbits was about 20 h, so roughly 10% is removed in 3 h; thus, the peak rate of liposomal cholesterol removal was about 2 umoles/h/kg, and this caused a subsequent rise in plasma cholesteryl ester concentrations. Notice that at other time periods after the injection, the rate of liposomal cholesterol removal from plasma was less. Note also that the liver is the predominant organ for clearance, but not the sole organ for clearance.

It has been calculated that a single injection of 300 mg LUVs/kg into 20–22-g mice mobilized about 2400 nmoles of cholesterol in the first 24 h after injection. In contrast to the data with SUVs in rabbits, the mobilization of cholesterol during the first 24 h in the mice injected with LUVs was quite steady. This calculates to about 4.7 μmoles/h/kg over this first 24-h period, which is actually more than the above figure of 2 μmoles/h/kg, which was a peak rate. It is not fair comparison, because the clearance of LUVs in mice is three times as fast as in rabbits. If we take 4.7 divided by 3, we get 1.6 umoles/h/kg, which is less than 2, but these are imperfect estimates. Human rates can be empirically determined. It is clear, however, that LUVs deliver their cholesterol at a steady rate, whereas SUVs make a brief, rapid push of lipid into the liver.

At body temperature, the most desirable liposomes are fluid within the confines of the bilayer, which is called the liquid crystalline state. Less desirable are liposomes in the gel state, which is less fluid.

It is understood that unesterified cholesterol stimulates macrophages to express more tissue factor, a substance known to provoke blood clots. This explains the presence of abundant tissue factor in rupture-prone plaques, which, when they rupture, expose tissue factor to plasma and provoke a clot that can occlude the vessel, causing a heart attack. This would be another example of an abnormal cellular function that may be reversed by removal of cholesterol by liposomes.

Several human conditions are characterized by distinctive lipid compositions of tissues, cells, membranes and/or extracellular regions. For example, in atherosclerosis, cholesterol (unesterified, esterified, and oxidized forms) and other lipids accumulated in cells and in extracellular areas of the arterial wall and elsewhere. These lipids have potentially harmful biologic effects, for example, by changing cellular functions and by narrowing the vessel lumen, obstructing the flow of blood. Removal of the lipids would provide numerous, substantial benefits. Moreover, cells, membranes, tissues and extracellular structures would benefit from composition and alteration that include increasing resistance to oxidation and oxidative damages, such as by increasing the content and types of anti-oxidants, removing oxidized material, and increasing the content of material that is resistant to oxidation. In aging, cells have been shown to accumulate sphingomyelin and cholesterol, which alter cellular functions. These functions can be restored in vitro by removal of these lipids and replacement with phospholipid from liposomes. A major obstacle to performing similar lipid alterations in vivo has been disposition of the lipids mobilized from tissues, cells, extracellular areas, and membranes. Natural (e.g., high-density lipoproteins) and synthetic (e.g., small liposomes) particles that could mobilize peripheral tissue lipids have a substantial disadvantage: they delivery their lipids to the liver in a manner that disturbs hepatic cholesterol homeostasis, resulting in elevations in plasma concentrations of harmful lipoproteins, such as low-density lipoprotein (LDL), a major atherogenic lipoprotein.

The invention described herein provides methods and compositions related to the "reverse" transport of cholesterol and other materials and compounds from peripheral tissues to the liver in vivo while controlling plasma LDL concentration.

Agarose gel electrophoreses of plasma samples from the last a set of rabbits injected with LUVs, SUVs, or saline (these agarose gels separate particles by their charge, which is not the same from one type of particle to another) were performed. Freshly made SUVs migrate very slowly through agarose, which indicates that freshly made liposomes have very little charge. After injection into animals or after co-incubation with plasma or lipoproteins, SUVs pick up proteins from lipoproteins. These proteins give more charge to the SUVs and substantially enhance their migration through agarose gels. SUVs after exposure to plasma migrate faster through these gels than does LDL.

The gels showed a substantial difference between LUVs and SUVs. As expected, the SUVs migrated ahead of LDL in these gels. The LUVs, however, migrated almost exactly where freshly made, protein-free liposomes migrate. This result indicates that LUVs, unlike SUVs, do not readily pick up proteins from circulating lipoproteins.

There is a direct verification of this difference between the liposomes. Human HDL (which has most of the proteins that liposomes pick up) was incubated with either LUVs or SUVs, then the liposomes were reisolated, and assayed their protein-to-phospholipid ratios. Per amount of liposomal phospholipid, the SUVs picked up about 40 times as much protein as did the LUVs. This difference appears to arise because of the difference in surface curvature: SUVs are smaller, so their surface is more tightly curved, thus under greater strain, proteins can more easily insert.

There are three most likely metabolic effects of the difference in protein uptake between the two types of liposomes are as follows:

1. VLDL has two metabolic fates: it can be removed from plasma before it is fully converted to LDL by lipolytic enzymes, or it can be fully converted into circulating LDL. SUVs strip apoE off VLDL, thereby slowing its clearance from plasma and favoring its conversion to LDL. In contrast, LUVs leave apoE on VLDL, and so LDL concentrations in plasma would not rise.

2. Absorbed apoproteins might play a role in directing liposomes to different hepatic metabolic pools.

Here are some ways to assay effect on oxidation in vivo: Catella F, Reilly M P, Delanty N. Lawson J A, Moran N, Meagher E, FitzGerald G A. Physiological formation of 8-epi-PGF2 alpha in vivo is not affected by cyclooxygenase inhibition. Adv Prostaglandin Thromboxane Leukot Res. 23:233–236, 1995. These authors describes 8-epi-PGF$_2$alpha, which is an end-product of lipid oxidation. This molecule can be used, they suggest, as a measure of lipid oxidative flux in an animal. It is superior to other commonly used measure of oxidation in vivo, such as antioxidant levels (which are affected by diet), thiobarituric acid reactive substances (some sugars interfere with this assay), and short-lived oxidative intermediates (these do not indicate total flux of material being oxidized). Administration of LUVs, by removing oxidized lipids from the periphery, would might lower total oxidative flux in vivo, and 8-epi-PGF$_2$alpha would be a suitable way to measure this; Cadet J, Ravanat J L, Buchko G W, Yeo H C, Ames B N. Singlet oxygen DNA damage: chromatographic and mass spectrometric analysis of damage products. Methods Enzymol. 234:79–88, 1994. they describe 8-oxo-2'-deoxyguanosine, which is an end-product of DNA oxidation. As above, this molecule can be used as a measure of DNA oxidative flux in an animal. Administration of LUVs would lower DNA oxidative flux in vivo, and this is a suitable way to measure this; and, Xia E, Rao G, Van Remmen H, Heydari A R, Richardson A. Activities of antioxidant enzymes in various tissues of male Fischer 344 rats are altered by food restriction. J Nutr. 125(2):195–201, 1995. Antioxidant enzymes in tissues were measured, to indicate de-oxidant capacity. LUVs help this. Anti-oxidant levels (vitamin E, ascorbate, urate); oxidized and reduced glutathione; and many other measures can be used to assess peripheral oxidation and oxidative damage. Again, these and other measures would be coupled with LUV administration, to assess efficacy of the therapy.

Other particles that mimic there properties of large liposomes will act similarly, to mobilize peripheral lipids and other exchangeable materials, and deliver exchangeable materials, while avoiding harmful disruptions in hepatic cholesterol homeostasis. For example, these would include emulsion particles that are two large to penetrate hepatic endothelial fenestrae, of a composition and structure that is taken up by the liver slowly, and/or a composition and structure that does not readily acquire specific endogenous proteins. Such emulsions could be made with or without proteins, and could be made from phospholipid and a neutral lipid, such as triglycerides or another neutral lipid. Angioplasty can of course be done on any blocked vessels, including but not limited to femoral arteries. Vessels upon which angioplasty can be done include, by way of example, arteries and veins. Exemplary arteries include vesical arteries, an iliac artery, an umbilical artery, an internal pudendal artery, an anterior humeral circumflex artery, a cerebral artery, an intercostal artery, a spinal artery, a temporal artery, a tibial artery, an ulnar recurrent artery, a coratid artery, etc. Exemplary veins include an ascending lumbar vein, an angular vein, a facial vein, a jugular vein, a tibial vein, etc.

While only a few, preferred embodiments of the invention have been described hereinabove, those of ordinary skill in the art will recognize that the embodiment may be modified and altered without departing from the central spirit and scope of the invention. Thus, the preferred embodiment described hereinabove is to be considered in all respects as illustrative and not restrictive, the scope of the invention being indicated by the appended claims, rather than by the foregoing description, and all changes which come within the meaning and range of equivalency of the claims are intended to be embraced herein.

I claim:

1. An improved method of angioplasty or cardiac catheterization in which said improvement comprises:

administering a therapeutically effective amount of a lipid acceptor to a subject, said lipid acceptor being selected from the group consisting of large liposomes comprised of phospholipids substantially free of sterol and small acceptors.

2. The method in accordance with claim 1 in which said administration of said lipid acceptor occurs at or over an effective period of time.

3. The method in accordance with claim 2 in which said effective period of time is in the range of about 1 minute to about two years from the time of said angioplasty or said cardiac catheterization.

4. The method of claim 1 in which said administration of said lipid acceptor occurs simultaneously with said angioplasty or said cardiac catheterization.

5. The method of claim 1 further comprising assessing a vascular function.

6. The method of claim 5 in which the step of assessing a vascular function is selected from the group consisting of measuring blood flow in a carotid artery, measuring blood flow in a lower limb, measuring blood flow in a vessel using ultrasound, measuring blood flow using an MRI, measuring blood flow using a radioisotope tracer, and measuring blood viscosity.

7. The method of claim 1 in which said angioplasty is performed on a blocked vessel.

8. The method of claim 7 in which said blocked vessel is selected from the group consisting a femoral vessel and a coronary vessel.

9. The method of claim 1 in which said angioplasty comprises carotid endarterectomy.

10. The method of claim 1 in which said angioplasty comprises surgery to relieve a carotid obstruction.

11. The method of claim 1 in which said angioplasty comprises a mechanical or a surgical intervention to improve blood flow.

12. The method in accordance with claim 11 in which said intervention comprises placement of a stent.

13. The method of claim 1 in which said angioplasty comprises coronary angioplasty, femoral angioplasty, and a surgery to relieve a carotid obstruction.

14. The method in accordance with claim 1 in which said large liposomes have diameters larger than about 120 nm.

15. The method in accordance with claim 1 in which the large liposomes have diameters larger than about 125 nm.

16. The method in accordance with claim 1 in which the large liposomes have diameters larger than about 150 nm.

17. The method in accordance with claim 1 in which the large liposomes have diameters larger than about 160 nm.

18. The method in accordance with claim 1 in which the large liposomes have diameters larger than about 175 nm.

19. The method in accordance with claim 1 in which the large liposomes have diameters larger than about 200 nm.

20. The method of claim 1 in which said large liposomes have an unesterified cholesterol to phospholipid molar ratio below about 1:10.

21. The method of claim 1 in which said large liposomes comprise POPC.

22. The method of claim 1 in which the large liposomes are given in repeated doses.

23. The method of claim 1 in which said phospholipids are given in a daily dosage of less than about 600 mg/kg body weight.

24. The method of claim 23 in which said dosage is administered repeatedly.

25. The method in accordance with claim 1 in which the large liposomes are made of phospholipids selected from the group consisting of phosphatidyl choline, phosphatidyl glycerol, palmitoyl-oleoyl phosphatidyl choline, and combinations thereof.

26. The method in accordance with claim 1 further comprising administering a lipid lowering drug.

27. The method in accordance with claim 1 further comprising administering a drug that inhibits restenosis.

28. The method in accordance with claim 1 further comprising inserting a device in a subject that inhibits restenosis.

29. The method in accordance with claim 28 in which said device comprises a stent.

* * * * *